(12) United States Patent
Vad et al.

(10) Patent No.: US 11,759,236 B2
(45) Date of Patent: *Sep. 19, 2023

(54) CARTILAGE REPAIR, PRESERVATION AND GROWTH BY STIMULATION OF BONE-CHONDRAL INTERFACE AND DELIVERY SYSTEM AND METHODS THEREFOR

(71) Applicant: Vad Scientific LLC, New York, NY (US)

(72) Inventors: Vijay Vad, New York, NY (US); Raghav Barve, Pune (IN); Paul Mulhauser, New York, NY (US); Karl D. Kirk, III, New York, NY (US)

(73) Assignee: Vad Scientific, LLC

( * ) Notice: Subject to any disclaimer, the term of this patent is extended or adjusted under 35 U.S.C. 154(b) by 0 days.

This patent is subject to a terminal disclaimer.

(21) Appl. No.: 17/681,768

(22) Filed: Feb. 26, 2022

(65) Prior Publication Data

US 2022/0280191 A1    Sep. 8, 2022

Related U.S. Application Data

(63) Continuation of application No. 16/862,448, filed on Apr. 29, 2020, now Pat. No. 11,389,196, which is a continuation of application No. 15/819,751, filed on Nov. 21, 2017, now abandoned, which is a continuation of application No. 13/861,360, filed on Apr. 11, 2013, now Pat. No. 9,827,010.

(Continued)

(51) Int. Cl.
*A61B 17/34*    (2006.01)
*A61M 5/158*    (2006.01)

(52) U.S. Cl.
CPC ......... *A61B 17/3472* (2013.01); *A61M 5/158* (2013.01)

(58) Field of Classification Search
CPC ........ A61M 2210/02; A61M 2039/025; A61B 17/3472; A61B 17/56; A61B 17/562; A61B 2017/564; A61B 2017/565; A61B 2017/567; A61B 2017/568; A61B 17/8805; A61B 17/8811; A61B 17/8816; A61B 17/8819; A61B 17/8833
See application file for complete search history.

(56) References Cited

U.S. PATENT DOCUMENTS

2013/0096492 A1*  4/2013  Lessing ................. A61M 1/77
                                                       604/35

* cited by examiner

*Primary Examiner* — Amber R Stiles
*Assistant Examiner* — Leah J Swanson
(74) *Attorney, Agent, or Firm* — Peter Materna

(57) ABSTRACT

Therapeutics and methods of treatment to repair, preserve and grow cartilage are presented. In addition, systems and methods for delivering a therapeutic to a hard to reach anatomical area, such as, for example, the BCI, are presented. A cannulated delivery device provided with a cutting tip, cutting flutes and threads on its distal end can be provided. Using such an exemplary device, various novel therapies for joint and cartilage repair, preservation and generation can be implemented. The device may have two-needles, with a first cannula/needle, with a finger grip at its distal end, and a longer inner needle to penetrate through the outer needle into the disc, and introduce therapeutics, for example, via a syringe. When provided with a septum at the inner needle's proximal end, the PIARES device is a completely closed system, and its use minimizes trauma.

15 Claims, 51 Drawing Sheets
(36 of 51 Drawing Sheet(s) Filed in Color)

Related U.S. Application Data

(60) Provisional application No. 61/800,574, filed on Mar. 15, 2013, provisional application No. 61/686,835, filed on Apr. 11, 2012.

FIG. 1A – EXAMPLE A POST-OP IMAGE

FIG. 1B – EXAMPLE A POST-OP IMAGE

PERCUTANEOUS INTRADISCAL ANNULAR REPAIR SYSTEM delivery device

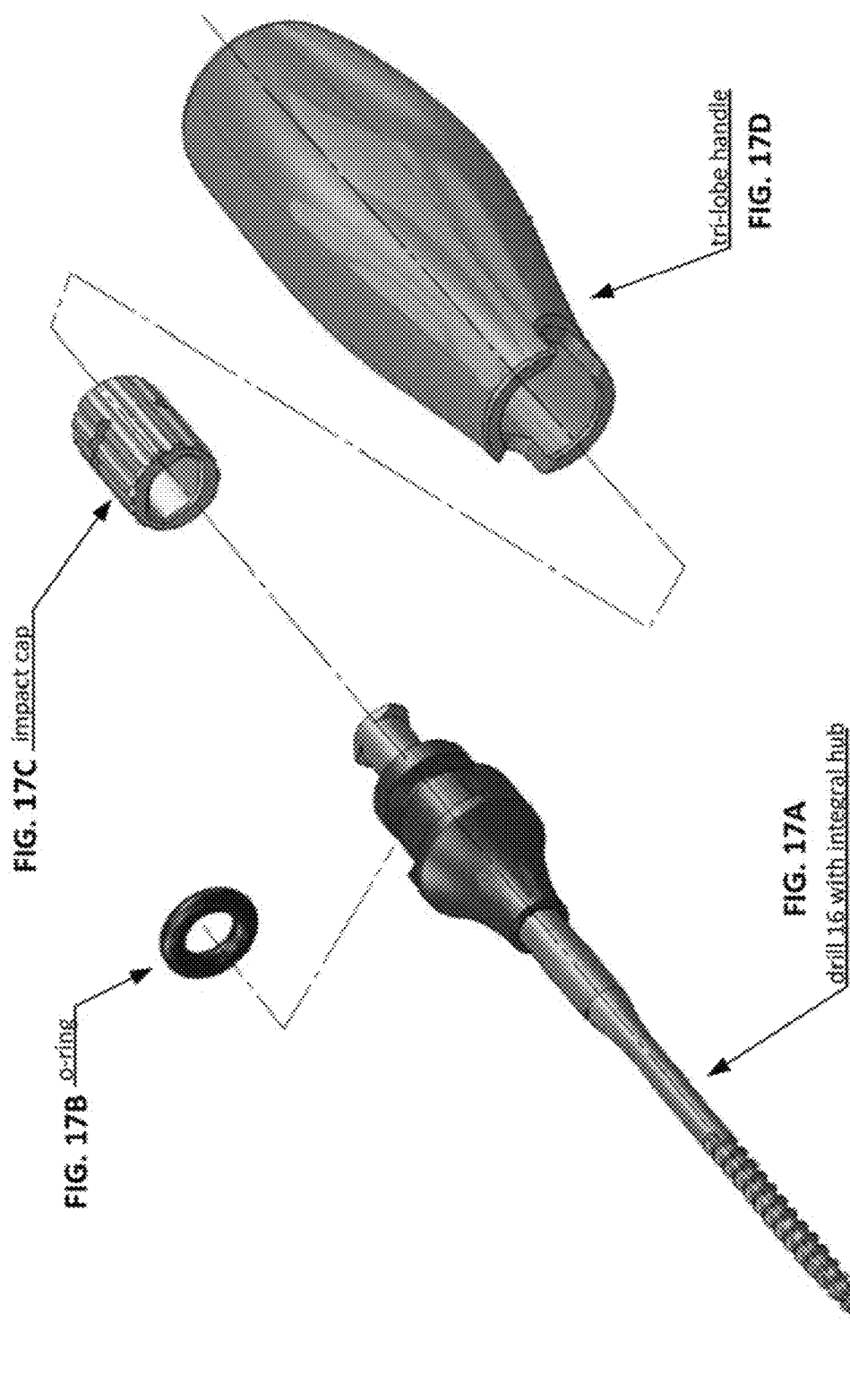

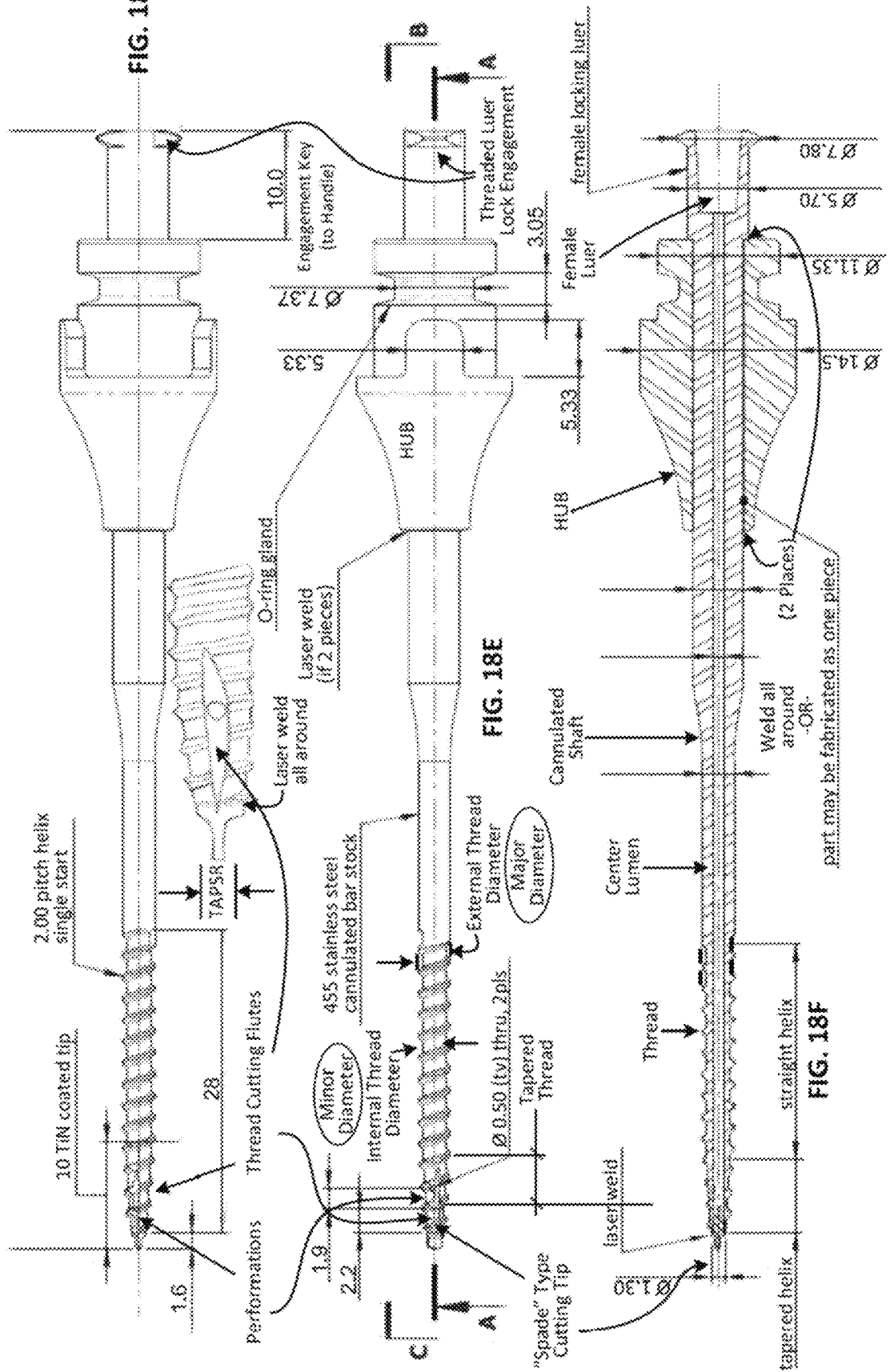

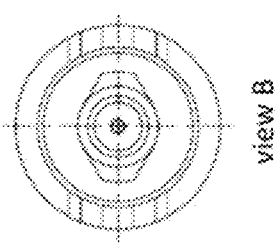
view B
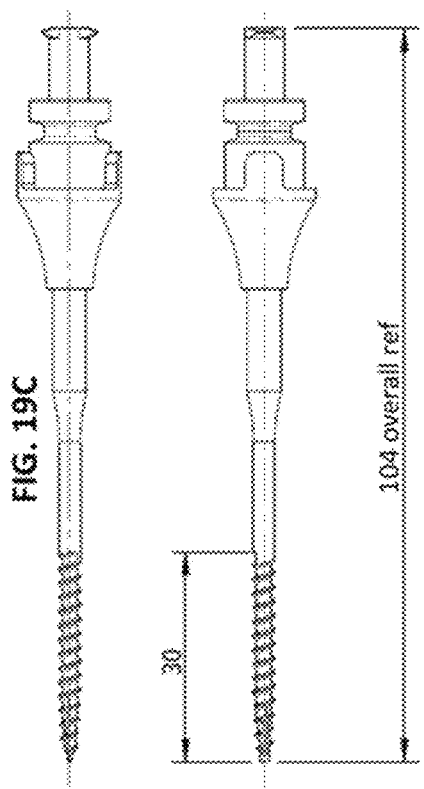
FIG. 19C
104 overall ref
30
⌀.145
view C
FIG. 19A
FIG. 19B
D
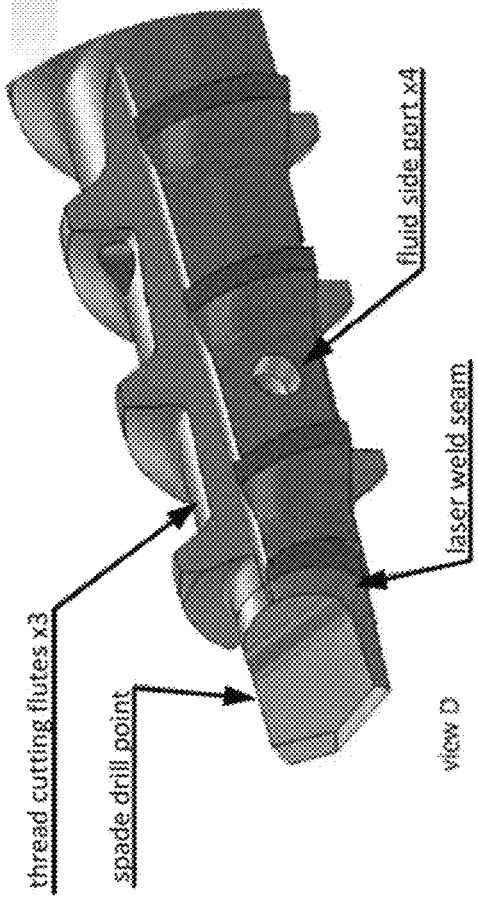
fluid side port x4
laser weld seam
thread cutting flutes x3
spade drill point
view D

CARTILAGE REPAIR, PRESERVATION AND GROWTH BY STIMULATION OF BONE-CHONDRAL INTERFACE AND DELIVERY SYSTEM AND METHODS THEREFOR

CROSS-REFERENCE TO RELATED APPLICATIONS

The present application is a continuation of U.S. patent application Ser. No. 16/862,448, filed Apr. 29, 2020, which is a continuation of U.S. patent application Ser. No. 15/819,751, filed Nov. 21, 2017, which is a continuation of U.S. patent application Ser. No. 13/861,360, filed Apr. 11, 2013, now U.S. Pat. No. 9,827,010, which claims priority to U.S. Provisional Patent Applications No. 61/686,835, filed on Apr. 11, 2012, and 61/800,574, filed on Mar. 15, 2013, each entitled "CARTILAGE REPAIR, PRESERVATION AND GROWTH BY STIMULATION OF BONE-CHONDRAL INTERPHASE AND DELIVERY SYSTEM AND METHODS THEREFOR". All of these are hereby incorporated herein by reference.

TECHNICAL FIELD

The present invention relates to various novel treatments for degenerative joints and discs, and improved devices and therapies for the delivery of therapeutic agents to hard to reach anatomical areas with minimal trauma so as to better implement such novel treatments.

BACKGROUND OF THE INVENTION

Conventional Therapies for Degenerative Disc and Other Cartilage Disease

Considering knee degeneration or osteoarthritis ("OA") as an example, pain in knee OA, defined as loss of articular cartilage in the knee, is thought to be caused by increased pressure on the subchondral bone. Thus, there are changes in subchondral bone marrow that can be seen at the earliest stages of the onset of OA (Lorieg et al, Rheum 7: 43-49, 2011). Current technologies for treating knee OA include non-steroidal anti-inflammatory drugs (Nsaids) including the newer Cox-2 inhibitors. Although these medications decrease inflammation and pain, their prolonged use (i) is thought to have an adverse impact on cartilage and (ii) comes with complications of increased risk of hypertension, coronary artery disease, renal failure (especially in diabetics) and peptic ulcer disease.

Hyaluronic acid (HA) has been shown to have some positive impact on cartilage. However, it has limited success rates in treating knee OA. Thus, while some studies show good success rates, others show rather poor ones. Furthermore, success rates decrease substantially in those patients with moderate to severe knee OA.

Microfracture has been used for a very small subset of knee OA patients with small cartilage defects. This technique has seen limited success rates. The technique functions by creating fibrocartilage. However, if done excessively, microfracture can sometimes even accelerate the rate of cartilage loss.

Finally, total and partial knee replacements have been used. These procedures have significant complication rates of blood clots and infections, are expensive, require hospital stays, have the associated liability of inserting metal in the body, and come with markedly increased healthcare costs.

Conventionally, when delivering a therapeutic agent to a hard to reach anatomical area, such as, for example, the bone-chondral interface (BCI), a drill is used to create a pathway. Generally, a device with a central cannula is used, which is initially provided with a miniature drill shaft and drill bit within it. The practitioner drills into the bone, and then removes the drill shaft and bit from the central cannula. Then a stylet is inserted, thus isolating the bone tissue from the outside environment. Finally, the stylet is removed and one of various appropriate therapies (e.g., drug, biologic or therapeutic) can be delivered via a syringe or other delivery device.

This conventional procedure thus twice exposes the internal tissue to ambient air. Once when the drill shaft and bit are removed and replaced with a stylet, and again when the stylet is removed to introduce a therapeutic agent. Each time internal tissues are exposed in this way the risk of infection increases. Furthermore, this is technically more challenging and time consuming with increased risk of complications.

What is thus needed in the art are exemplary devices and methods to reach internal anatomical areas which at the same time decreases the exposure of internal tissues to ambient air and reduces trauma. What are further needed in the art are therapeutics and methods of treatment to address loss of cartilage, and devices that enable simpler delivery of such therapeutics in less time, with reduced trauma, so as to reduce the risk of complications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B, are a set of two images entitled "Example A Pre-operative" and "Example A Post-operative" from an example test case according to an exemplary method of the present invention, described below as "Example A" under the Experimental Results portion of this disclosure. These images relate to the case described in the independent radiologist's report provided in Appendix A.

FIG. 17A depicts a drill portion of the exemplary delivery device of FIG. 16A;

FIG. 17B depicts an exemplary o-ring of the exemplary delivery device of FIG. 16A;

FIG. 17C depicts an exemplary impact cap of the exemplary delivery device of FIG. 16A;

FIG. 17D depicts a tri-lobe handle of the exemplary delivery device of FIG. 16A;

FIGS. 18D, 18E and 18F depict magnified views of FIGS. 18A, 18B and 18C, respectively, with additional detail;

FIG. 19A depicts top and bottom views of the exemplary device of FIGS. 18A and 18B;

FIG. 19B depicts solid perspective views of the exemplary device of FIG. 19A;

FIG. 19C depicts a magnified view of the tip of the exemplary device of FIG. 19B;

SUMMARY OF THE INVENTION

Figure 1C:
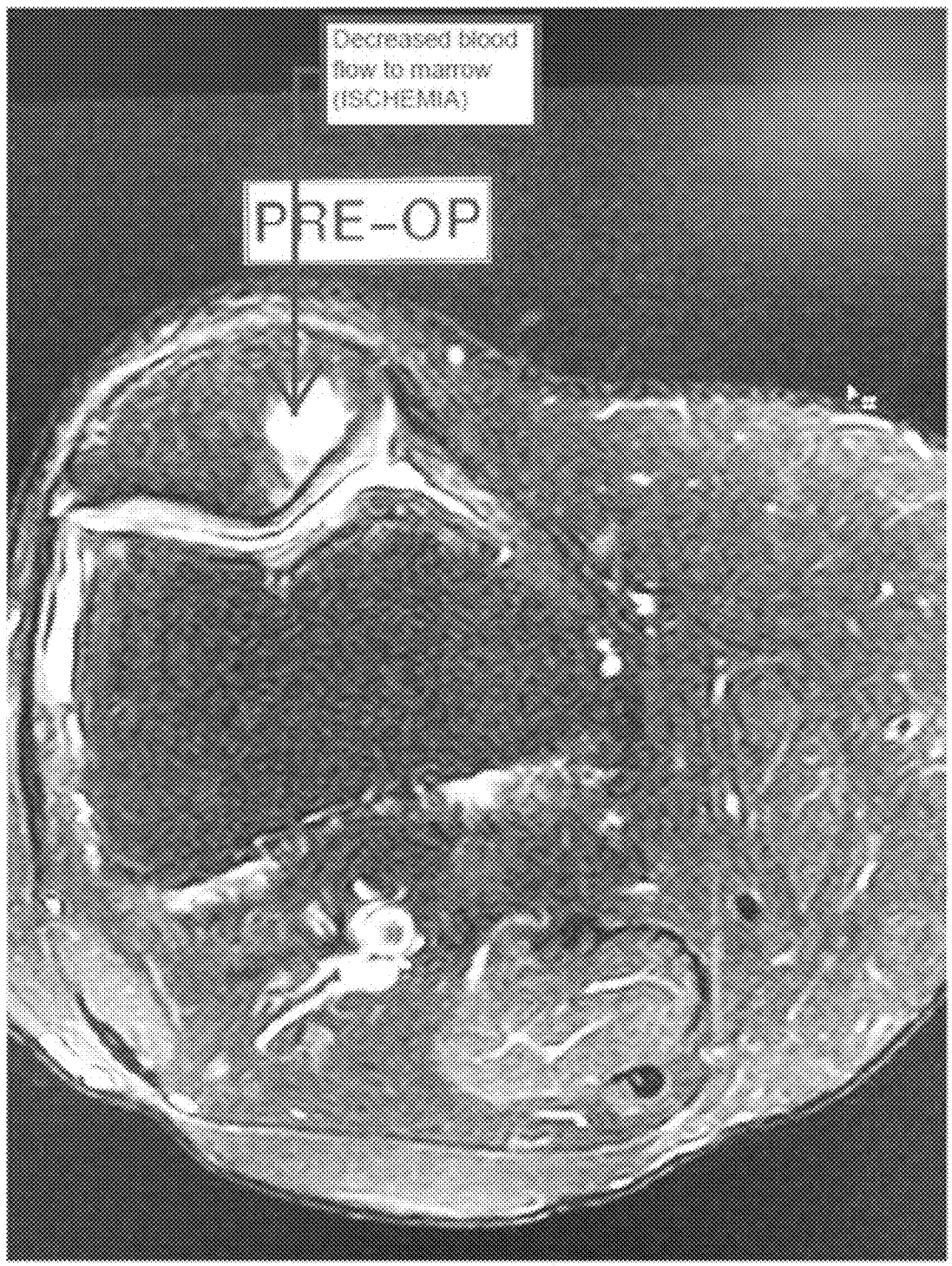
FIGS. 1C and 2 are preoperative scans of an individual's knee.

Novel therapeutics and methods of treatment to repair, preserve and grow cartilage are presented. In addition, systems and methods for delivering a therapeutic to a hard to reach anatomical area, such as, for example, the BCI, are presented. In exemplary embodiments of the present invention, a cannulated delivery device provided with a cutting tip and threads on its distal exterior can be provided which has considerable advantages over conventional devices. These include, for example, (i) ease of manufacture, (ii) use of the exemplary device being faster than conventional approaches, with both less table time and less steps, (iii) lesser exposure of internal tissues to ambient air, and thus less risk of infection, and (iv) lesser technical complexity leading to lesser complications. Using such an exemplary device, various novel therapies for joint and cartilage repair, preservation and generation can be implemented. Various versions of such a device are disclosed. Alternatively, for disc repair, a delivery device directed to percutaneous intradiscal annular repair, or "PIARES" device can be used to introduce therapeutics intradiscally. The device is a two-needle device, with a first cannula/needle, with a finger grip at its distal end, and a longer inner needle, which can then penetrate through the outer needle into the disc, and can then, for example, be used to introduce therapeutics, for example, via a syringe. When provided with a septum at the inner needle's proximal end, the PIARES device becomes a completely closed system, and its use minimizes trauma.

Thus, in exemplary embodiments of the present invention, a surgical hand tool can be provided, used for the non-invasive placement and delivery of therapeutics, to a targeted site. This can be done through minimally invasive skin incision, or without any incision, as may be desired. The delivery and placement of the therapeutic can be controlled and does not need a powered drill or guide wire.

An exemplary device can have a closed pointed end, a threaded portion, and be provided with thread cutting/forming features, such as flute(s), and can have a shaft perforations to the central lumen at a distal end to deliver therapeutics or other preparations. At the proximal end, means can be provided to attach a syringe in communication with the shaft's central lumen, and there may be a keyed engagement feature for attachment of a hand grip. The delivery device can be made of sufficient length to reach bone on either side of a desired or targeted joint, and to easily penetrate soft tissue and cortical bone to reach a targeted site in cancellous bone adjacent to a cartilage defect.

The device's main shaft or drill portion can be made of hardened stainless steel, or the like, such as, for example, 400 series or 17-40 stainless steel, for example.

The device can have, for example, an attachable/removable hand grip for ease of placement of the drill bit to a site, with a solid proximal end with which to tap or hammer, and with a grip for torquing the device through cortical bone and to guide a threaded shaft to a targeted site in cancellous bone, for example. The grip can have an ergonomic form for ease of use, such as a tri-lobe handle, which mimics the natural turn of a wrist in 120 degree increments.

The device can have an impact cap to (i) provide impact anvil surface to protect a proximal luer during impaction, as well as to (ii) close the luer opening to a shaft lumen.

DETAILED DESCRIPTION OF THE INVENTION

While the exact cause of knee OA remains unknown, it is strongly believed by the inventors that alterations in the bone-cartilage interface ("BCI") are present at the earliest stages of knee OA. Therefore, therapies for treating knee OA must target the BCI. This approach can further be extended to other areas where cartilage has been damaged or lost.

As described below, methods according to exemplary embodiments of the present invention address the BCI where early alterations can accelerate knee OA. In exemplary embodiments of the present invention, methods are provided to stimulate the subchondral bone marrow and expose the mesenchymal stem cells (MSCS) that come out of the bone marrow as a result, to growth factors from platelet-rich plasma (PRP) and very small embryonic like cells (VSELs). VSELs are known to be released after an injury resulting in enhanced repair in the animal stroke model (Kucia et al: Cell Tissue Research 331: 125-134, (2008). This enhances cartilage repair and possible regeneration. As is known, MSCSs exposed to PRP differentiate into chondrocytes (Mishra, et al: Tissue Eng. Methods 15: 431-435 (2009)).

Methods according to exemplary embodiments of the present invention have a very low risk of infection, are significantly less expensive than major surgical procedures, and avoid the liability of metal implants or NSAID medications. Furthermore there is very little down time for patients undergoing this procedure inasmuch as it is performed on an outpatient basis with a quick return to work.

I. Exemplary "Ground Up" Methodology for Cartilage Repair

In exemplary embodiments of the present invention, cartilage issues can thus be treated from the "ground up." Such an approach is analogous to how in agriculture plants are often treated by accessing their roots. Thus, in exemplary embodiments of the present invention, technologies can be used that target the bone-cartilage interface (BCI) to treat cartilage issues, as opposed to conventional "top down" approaches such as, for example, the current undesirable practice of microfracture. As noted above, microfracture creates fibrocartilage with very limited success in patients with cartilage defects. Moreover, microfracture can only be used for a very small subset of knee osteoarthritis ("OA") patients-only those having small cartilage defects. If it is done excessively it itself can even lead to accelerated cartilage loss.

Thus, in exemplary embodiments of the present invention, novel methodologies for the treatment of degenerative joints and discs can be utilized. This can be applied, for example, to the knee, to treat medial joint knee degenerative disc disease ("DJD") using the following protocol, for example:

Day 1:
350 mcg of Granulocyte Colony-Stimulating Factors ("GCSFs") injected subcutaneously;

Day 2:
350 mcg of Granulocyte Colony-Stimulating Factors, or GCSFs injected subcutaneously (this second GCSF injection is optional);

Draw blood and spin it down to obtain 4 cc of Platelet Rich Plasma ("PRP") in total;

Put 1 cc of the PRP into the tibial medial compartment by drilling and injecting at the bone-cartilage interface ("BCI"), followed by injection of 0.1 cc of 10% calcium chloride solution or thrombin to form a clot.

Wait two minutes before reverse drilling out the delivery device so that a clot may form and keep the PRP from leaking out. Alternatively, bone wax can be injected to keep the PRP in place;

Put 1 cc of PRP into femoral medial or lateral compartment by drilling and injecting at the bone-cartilage interface, followed by injection of 0.1 cc of 10% calcium chloride solution or thrombin to form a clot.

Wait two minutes before reverse drilling out the delivery device so that a clot may form and keep the PRP from leaking out;

Put remaining 2 cc PRP into the knee joint;

MRI is done pre-treatment and at 3 months post-treatment.

It is understood that these are exemplary values only. Variations of the quantities of therapeutics can also be used, such as, for example, a range of 1-3 cc of PRP injected each above and below the relevant joint, a range of 0.1-0.3 cc of calcium chloride used afterwards, and a range of 2-6 cc of PRP injected into the joint. Additionally, one can wait between 2-4 minutes following delivery of the PRP and clotting agent, for example.

It is noted that GCSFs have not heretofore been used for cartilage repair. An exemplary GCSF that may be used can be, for example, Neupogen.

In exemplary embodiments of the present invention, the PRP can be delivered via one syringe, and either CaCl, thrombin or bone wax, for example, can be delivered via another syringe. Alternatively, a skilled, dexterous and quick practitioner may, for example, load both the PRP and CaCl into one syringe, if she can deliver the dose quickly enough so that no clotting occurs. In exemplary embodiments of the present invention this method can be used, and the inventors have successfully done it in experimental cases.

In exemplary embodiments of the present invention the procedure can, and preferably should, be performed under fluoroscopy or ultrasound guidance to insure proper positioning of the delivery devices at the BCI and to further insure that there is no penetration through the cartilage, which would cause damage.

Following injection of the therapeutic, the delivery device should be left in place for approximately 2 minutes to make sure a clot is formed. Alternatively, bone wax or the equivalent can be used, for example, to seal the entry instead of calcium chloride.

Exemplary Sterile Kit

In exemplary embodiments of the present invention, an exemplary kit can contain, for example, two disposable delivery devices, to be used to inject at the BCI in the superior and inferior locations to a joint, as shown, for example, in FIGS. 23-48. Making them disposable minimizes the risk of infection. Such an exemplary kit can also be provided with a vial of bone wax and a 2 cc vial of 10% calcium chloride solution, for example. Calcium chloride activates platelets and also forms a clot. In general, the CaCl can be provided in a 1/10 ratio to the biologic, thus for 1 cc of stem cells and PRP, a 0.1 cc volume of CaCl may be used. Alternatively, in exemplary embodiments of the present invention, the delivery device may be reusable, and sterilizable, such as a version of the exemplary PecaBoo device described below. Still alternatively, a device can have a disposable hub and drill portion (including impact cap—see FIG. 17), and a reusable handle, for example.

Rationale—Expose Mesenchymal Cells to PRP to Generate New Cartilage

The rationale behind the inventive protocol is that bone marrow may be stimulated by the GCSFs to produce mesenchymal cells (MSC). As these MSC cells come out of the bone marrow and make their way towards the BCI, they are exposed to the PRP (or, for example, PRP and VSELs) before reaching the bone-cartilage interface. There is good evidence that exposure to PRP (or PRP and VSELs) induces the MSCs to become cartilage, or more granularly, the MSCs and VSELs (Very Small Embryonic Like stem cells), when exposed to PRP or hyaluronic acid develop into chondrocytes, which in turn create the cartilage matrix. This is believed to be the key factor that has led to the success seen in the knee treated and described in Appendix A, where an approximate doubling of cartilage size (relative to the pre-treatment MRI result) was seen in a post-operative MRI three months following treatment, with markedly reduced pain. Furthermore, VSELs are released into the peripheral blood following stimulation with GCSF which, as noted above, helps with cartilage repair. Thus, both PRP and VSELs ma, for example, be delivered to the femoral and tibial compartments, for example, in an exemplary knee procedure. Sometimes just drilling is sufficient to stimulate cartilage growth, or to resolve an ischemia. Thus, in various exemplary embodiments of the present invention, the following various approaches can be used in treating affected joints; in all cases a drill delivery device according to the present invention may be used:
1. Drill alone;
2. Drill+PRP+bone wax;
3. Drill+PRP+bone wax;
4. 300 mcg GCSF in 1-3 injections, then followed by drill, then followed by VSEL+PRP+{bone wax or CaCl};
5. Bone marrow aspirate+CaCl or bone wax;
6. Culture expanded autologous stem cells, from stem cell bank;
7. Autologous embryonic stem cells, from cord blood;
8. embryonic stem cells, from a cell bank; and
9. Autologous preserved cells.

Thus, in exemplary embodiments of the present invention, there can be a significant reduction in the number of knee replacements being done with a concomitantly large reduction in health care costs, inasmuch as the inventive technology does not involve hospitalization or expensive artificial joints. In exemplary embodiments of the present invention, if partial results are seen with one treatment, there is the option to repeat the treatment from three months to two years later for additional therapeutic benefit. It is noted that the treatment can be, for example, repeated indefinitely as long as there is therapeutic benefit. Thus, from some patients the treatment can be repeated over decades if helpful.

It is noted that in exemplary embodiments of the present invention the bone marrow can be, for example, chemically stimulated with GCSF, while the bone marrow can also be stimulated mechanically by creating microtrauma above the bone marrow ("above" in the sense of a direction towards the knee joint). Such a microtrauma stimulates the bone marrow to produce more MSCS and VSEL cells, and also increases the blood supply to the bone-cartilage interface to allow for better repair.

EXPERIMENTAL RESULTS

Example A

In an experimental trial of treatment methods according to an exemplary embodiment of the present invention, a 50 year old female with advanced degenerative osteoarthritic disease of the knee was treated. Prior to the treatment, a pre-operative MRI was done. Post treatment a three month follow-up MRI was performed on the patient and read by an independent radiologist. Provided hereto as Appendix A is the independent radiologist's report. As noted in the report, the post operative MRI showed an increase in cartilage matrix from 1.8 mm pre-treatment to 3.7 mm at the follow-up MRI. Thus, the inventive technique shows early promise for cartilage repair and possible regeneration.

Example B

Figure 2:
Figure 3:
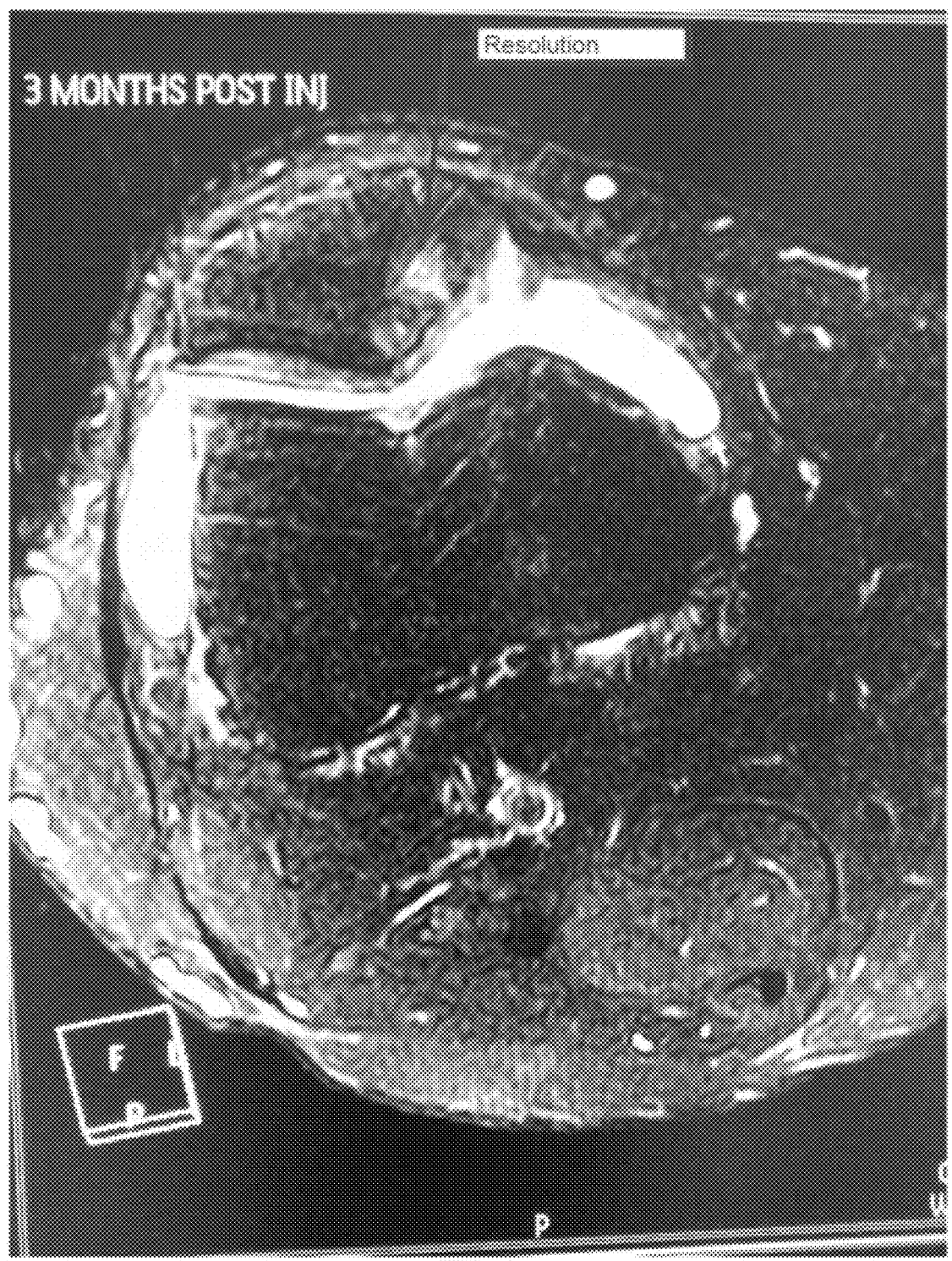
FIGS. 3-4 are corresponding scans of the individual's knee after treatment according to the methods of exemplary embodiments of the present invention.
Figure 4:

Imaging data from another experimental case are provided in FIGS. 1-4. As can be seen therein, FIGS. 1 and 2 are respectively axial and sagittal images of a patient's knee from a preoperative scan. FIG. 1 depicts an area of decreased blood flow due to an ischemia, as shown by the red arrow, also seen in FIG. 2 pointed to by the red and green arrows. Injections similarly performed according to the above described protocol, to the femoral and tibial compartments by drilling and injecting at the bone-cartilage interface, followed by injections into the knee joint. FIGS. 3 and 4 are corresponding axial and sagittal images form a MRI taken three months following the treatment. As can be seen, significant new cartilage has grown, and the ischemia has been essentially resolved, as shown in FIG. 3.

Example C

Figure 5:
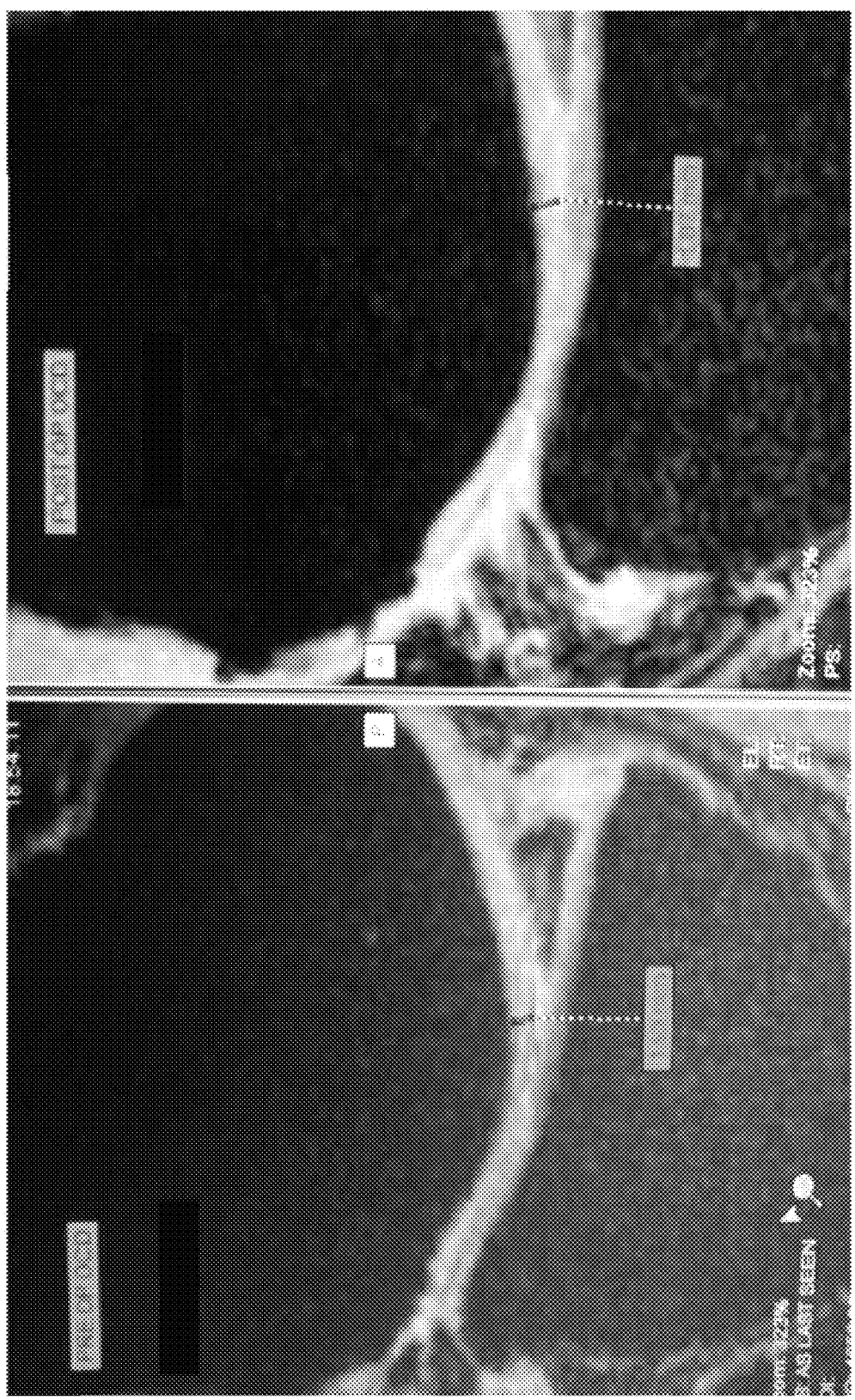
FIG. 5 is a side-by-side comparison of another individual's knee before and after treatment according to the methods of exemplary embodiments of the present invention.

FIG. 5 depicts side by side comparisons of sagittal images of a knee of a third patient. The left panel is an image form a preoperative scan, and the right panel a corresponding image from a post operative MRI. As shown in FIG. 5, the post operative MRI showed an increase in cartilage matrix from 1.60 mm to 1.87 mm at the follow-up MRI.

In exemplary embodiments of the present invention, the therapeutic protocol described above can similarly be used for osteoarthritis and avascular necrosis, as well as for treating meniscal and labral injuries in the joints.

Exemplary Variations of the Protocol

In exemplary embodiments of the present invention, variations on the above-described protocols can be used for other anatomical areas. Examples of these are next described.

Joints—for joints, the step of injecting GCSF for stimulating bone marrow may be skipped. The drilling/twisting alone of the delivery device (as described below) will stimulate bone marrow combined with PRP injection or injection of other biologics such as, for example, stem cells as an alternative.

Joint Arthritis—there is an alternative method for treating joint arthritis by using adipose tissue derived stem cells that can be injected intravenously combined with intra-articularly without drilling into the bone-cartilage interface. If that does not work then an alternative method is adipose derived stem cells injected intravenously, intra-articularly and into the bone-cartilage interface. This combination of systemic and local therapy is believed to be the next big step in biologic interventions for joint issues.

Spine—in similar fashion as was described above for the knee, for the spine one can inject GCSF on days 1 and 2, followed by extracting PRP on day 2. The PRP can then be drilled into vertebral bodies above and below the affected disc along with intra-discal injection and epidural injection of the PRP.

Figure 10:
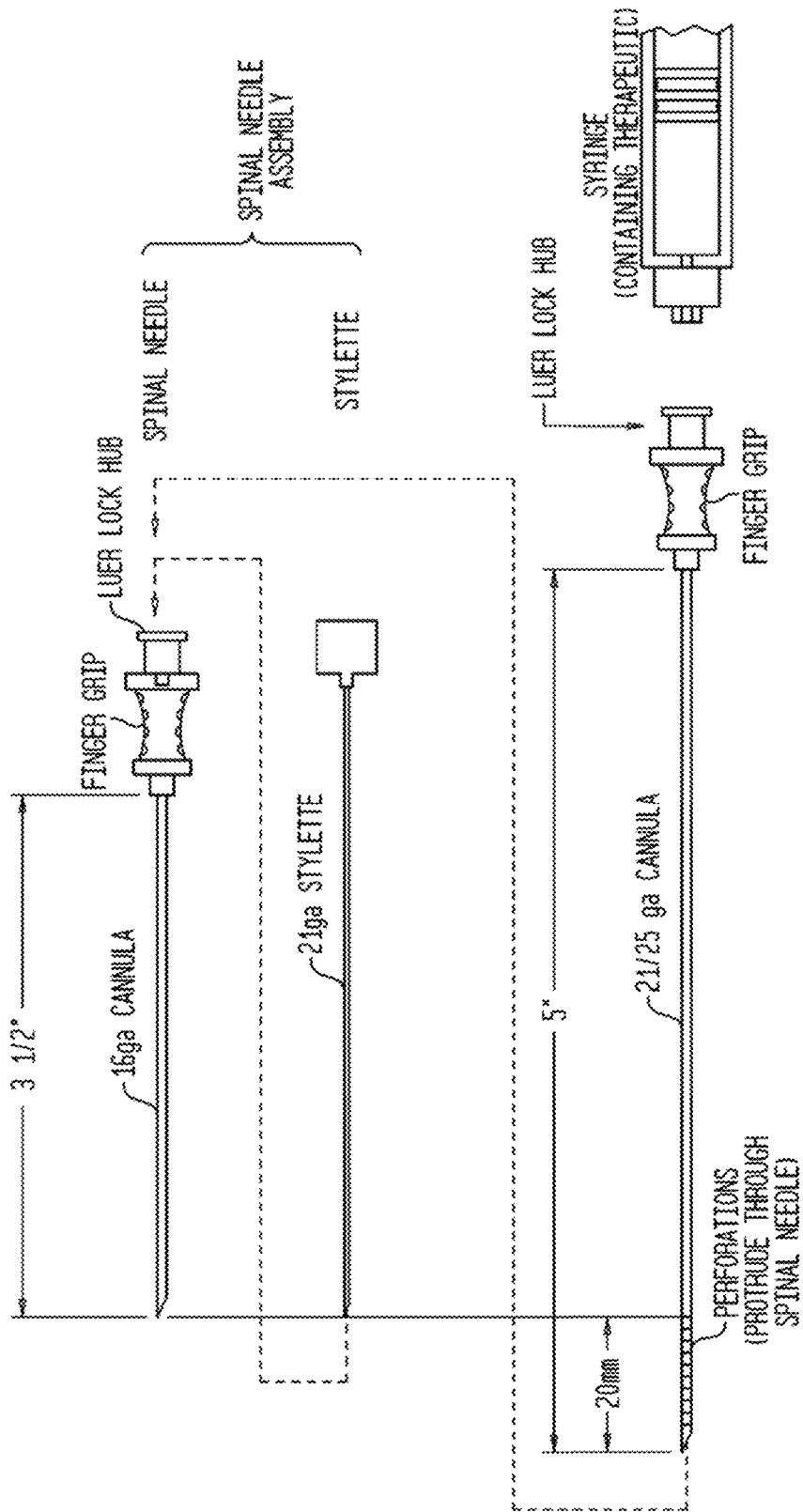
FIG. 10 depicts an exemplary delivery device which may be known as a "Percutaneous Intradiscal Annular Repair System" (PIARES"), directed to percutaneous intradiscal annular repair according to exemplary embodiments of the present invention.
Figure 11:
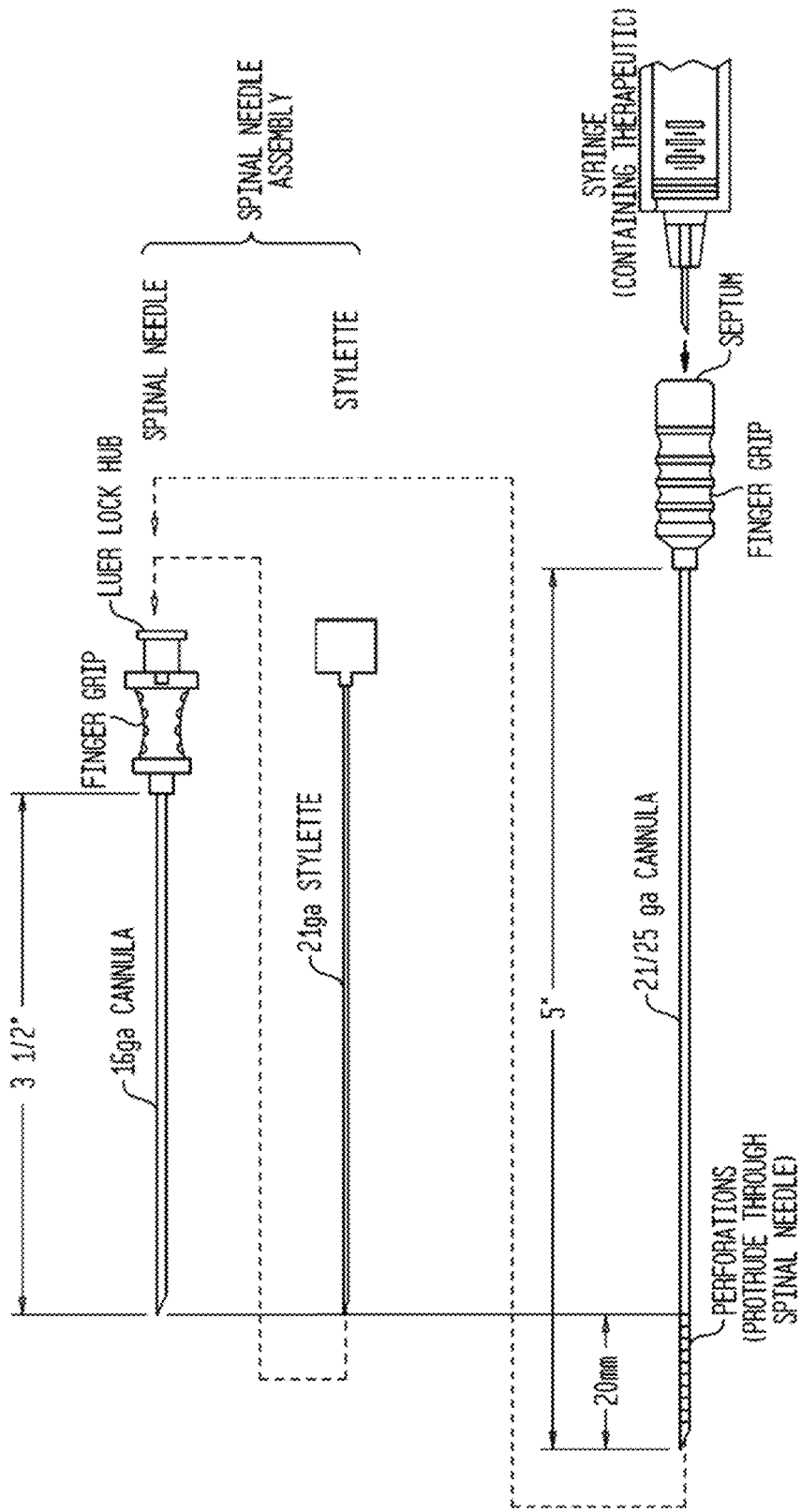
FIG. 11 depicts a variant embodiment of the exemplary delivery device of FIG. 10.

Alternatively, one can skip the GCSF and just drill into vertebral bodies followed by injection of PRP into the vertebral body followed by thrombin or calcium chloride to form a clot (so that the PRP does not leak out), and then injecting the PRP, followed by thrombin or calcium chloride, intradiscally. It is noted that for injecting the vertebral body the novel BCI device described below (FIGS. 6-8 and 12) can be used. For an intradiscal injection, standard existing spinal needles can be used, or for example, a variation of the novel PIARES delivery device as shown in FIGS. 10 and 11.

Finally, another alternative method for treating disc or stenosis issues of the spine can be, for example, to use adipose tissue derived stem cells which first can be given intravenously along with caudal epidural injection. If this does not give results, then the adipose stem cells can, for example, be given intravenously along with intradiscal injection and caudal epidural, using, for example, a standard spinal needle, or, for example, a variation of the novel PIARES delivery device as shown in FIGS. 10 and 11.

II. Exemplary Delivery Devices

In exemplary embodiments of the present invention, the therapeutic methods described above can be delivered in a safe and efficient manner using various novel delivery devices according to various exemplary embodiments of the present invention, as next described.

Exemplary Delivery Device

Figure 6:
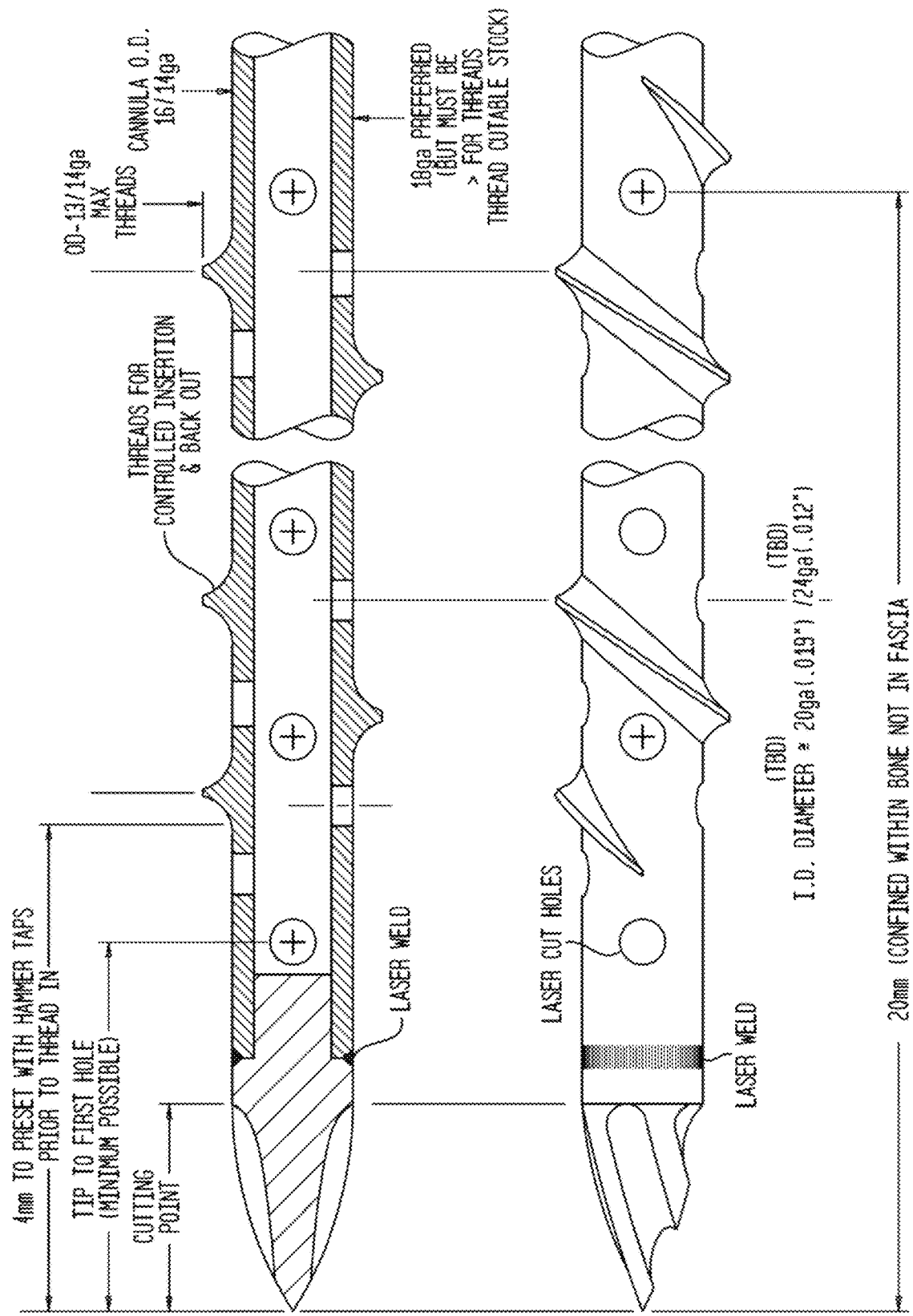
FIG. 6 is an exemplary distal end of an exemplary bone-chondral interface ("BCI") delivery device according to exemplary embodiments of the present invention.

FIGS. 6-9 depict an exemplary delivery device according to exemplary embodiments of the present invention. FIG. 6 depicts an exemplary distal end of an exemplary delivery device according to exemplary embodiments of the present invention. As can be seen therein, the device is essentially a hollow cannula with threads on the outside of it. The threads allow for controlled insertion and removal of the device. It has a cutting point at its distal end, and immediately proximal to the cutting tip (i.e., above it) a series of holes are provided to dispense various therapeutics. As shown in FIG. 6, the solid slug at the tip of the device can be laser welded in place, for example, and the various holes in the cannula laser cut, for example. Exemplary dimensions are shown in FIG. 6, but are understood to be merely exemplary, and not limiting.

Given the solid cutting tip, a user first presets the device with hammer taps, and then can screw in the device a desired length. This can be done manually, or via a drill interface provided at the distal end of the device, for example. As described below, one can, for example, tap with a hammer to set the device into place into dense cortical bone, and then subsequently twist (or drill) to advance the delivery device into spongy bone (interior cancellous bone).

Figure 7:
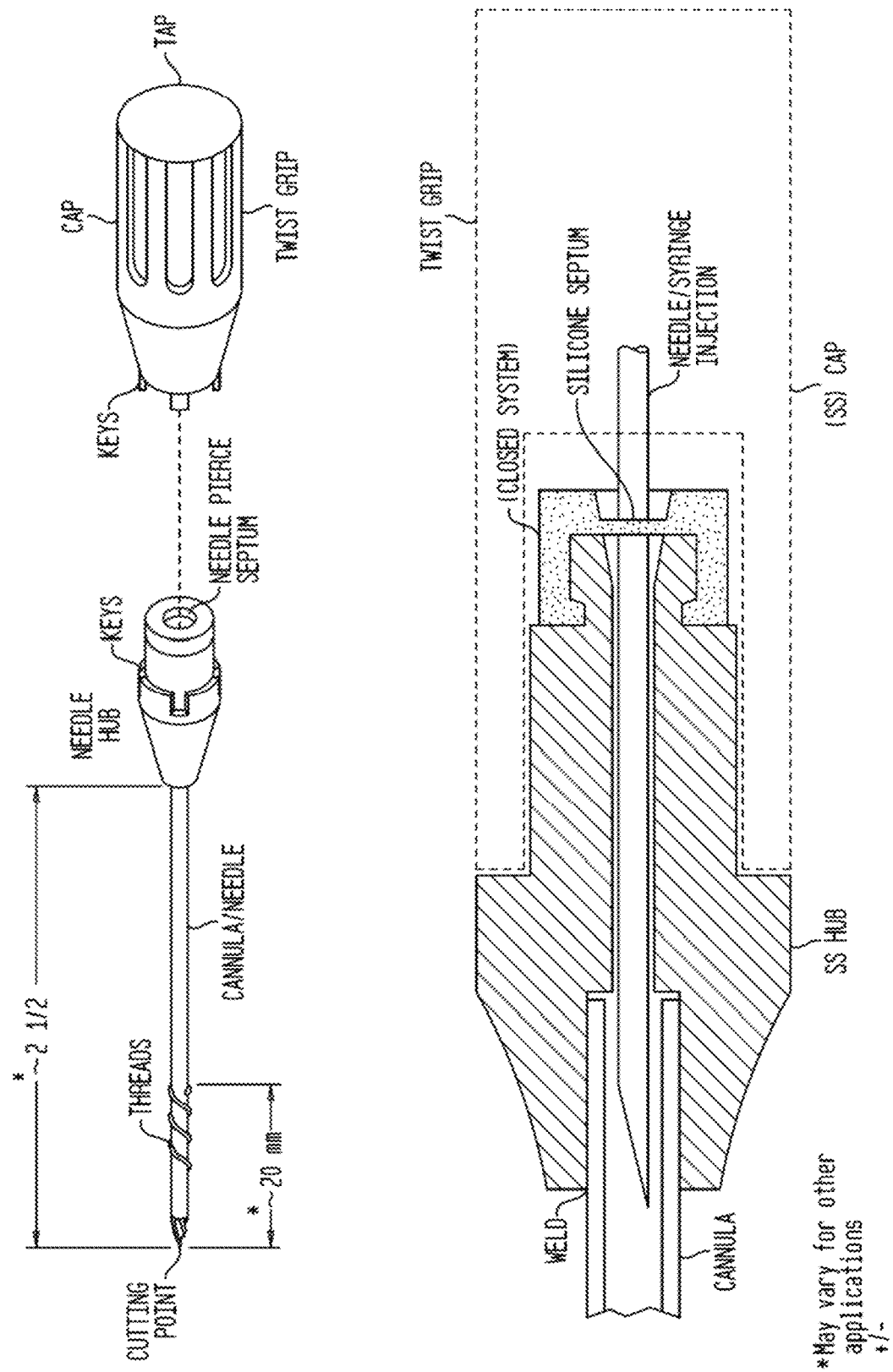
FIG. 7 is an exploded view of an exemplary delivery device according to exemplary embodiments of the present invention (top panel), and a magnified view of an exemplary proximal portion of the exemplary delivery device (bottom panel)

FIG. 7 is an exploded view of an exemplary embodiment of the delivery device according to the present invention (top panel), and a magnified view of an exemplary proximal portion of the exemplary delivery device (bottom panel). With reference thereto, the top panel of FIG. 7 shows how the device has a cannula/needle portion, a needle hub, and a cap with twist grip and a surface at its end for tapping with a hammer. The cap and needle hub can be connected via keys, which thus insure that the cap and needle hub do not move relative to one another as a user drills, for example, or manually screws/twists in, for example, the device.

Provided at the top of the needle hub can be a needle pierce septum, which allows a sterile syringe to be introduced into the cannula to inject therapeutics or PRP rich blood, as described above, after removing the cap, once the device is in the proper position. Thus, using such a septum, the tissue exposed to the distal end of the delivery device need never contact open air, and the delivery system is thus totally closed. The septum can be made of silicone, for example, or other appropriate materials.

Figure 8:
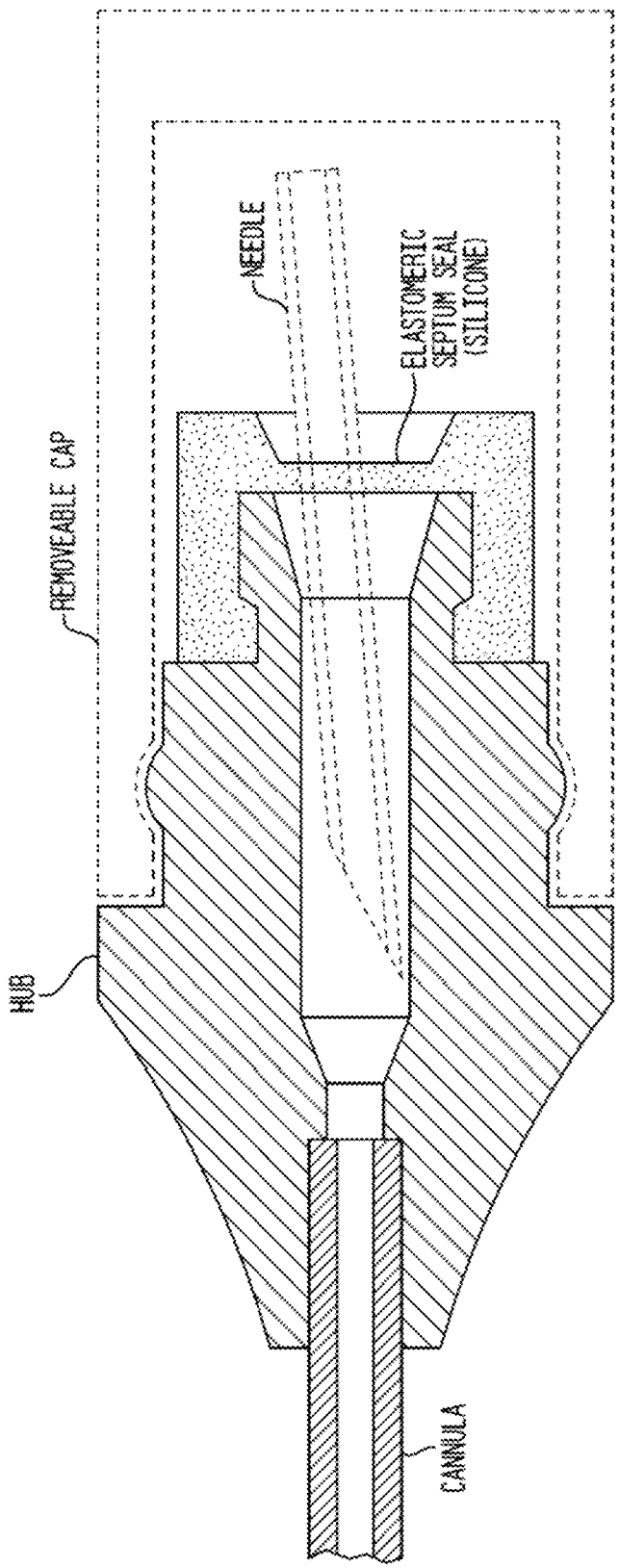
FIG. 8 is a further magnified view of an exemplary proximal portion of the exemplary delivery device of FIGS. 6-8.
Figure 9:
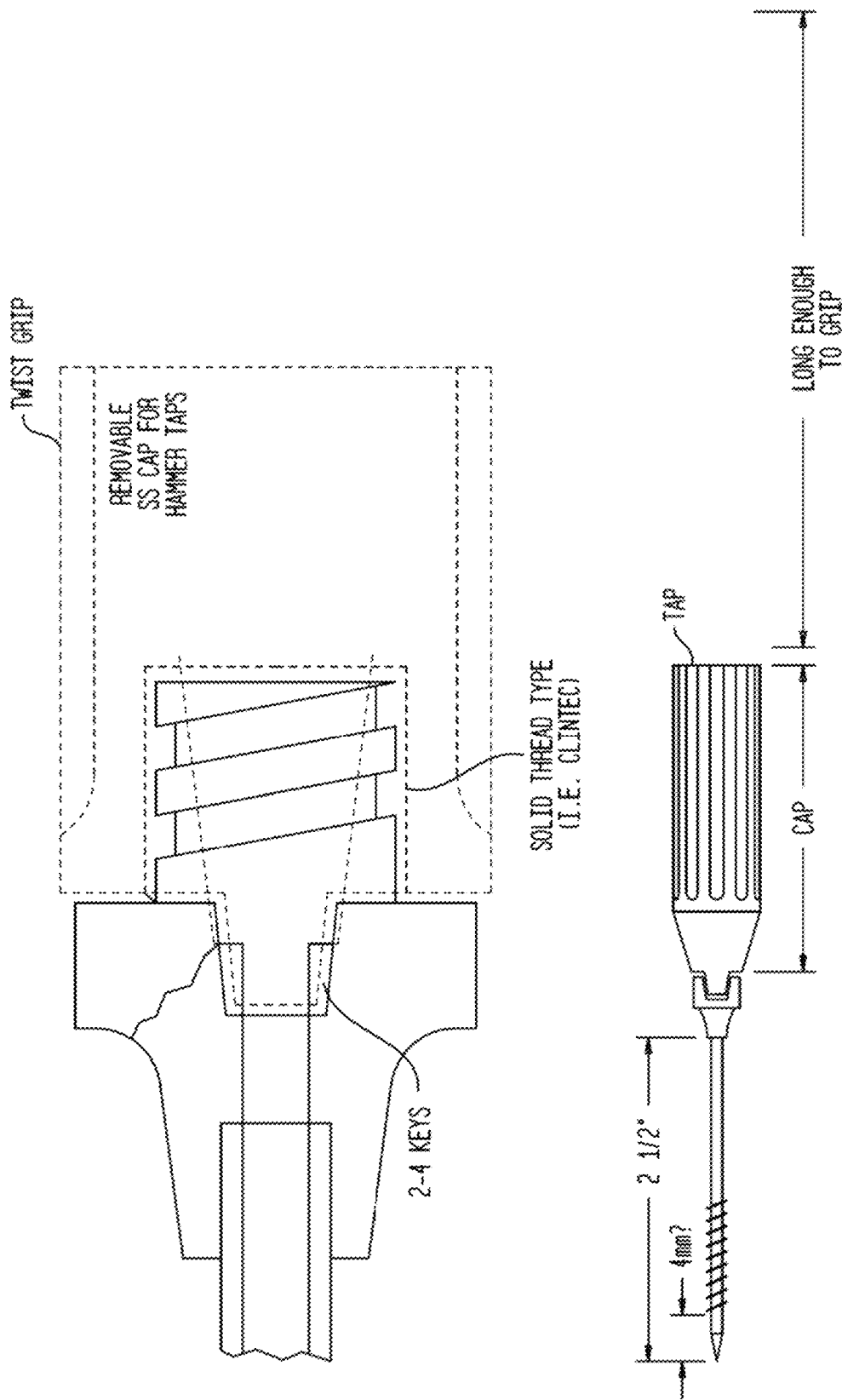
FIG. 9 depicts an alternate exemplary embodiment of the exemplary delivery device of FIG. 6.

FIG. 8 is a further magnified view of the distal portion of the exemplary device of FIG. 7. FIG. 9 depicts an alternate exemplary embodiment of an exemplary delivery device of FIG. 7, where the cap is screwed on to a luer provided at the distal end of the cannula/needle.

Exemplary Delivery Device For Discs—PIARES

Figure 12:
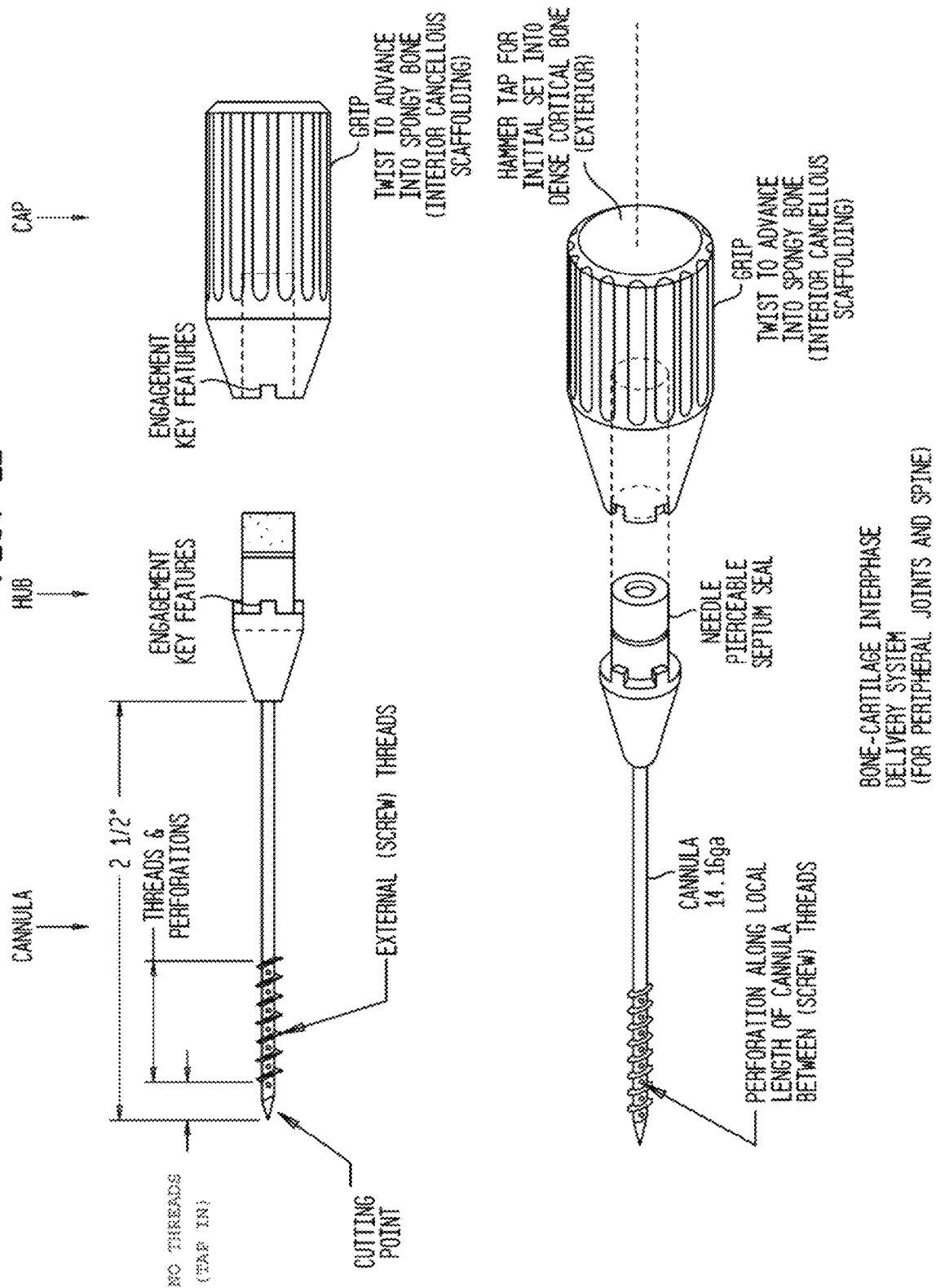
FIG. 12 depicts detailed views of an exemplary delivery device according to an embodiment of the present invention directed to bone-cartilage interfaces of peripheral joints and spine.

FIGS. 10-12 depict an exemplary delivery device directed to percutaneous intradiscal annular repair according to exemplary embodiments of the present invention. This device is known as a "PIARES" device by the inventors, and is used for introducing therapeutics intradiscally, as described above. Such a device is inserted by hand, in most cases. The device is a two-needle device, and can have, for example, a first cannula/needle, with a finger grip and luer hub at its distal end. The cannula can be, for example, 16 gauge, and be approximately 3.5 inches long, for example, but such dimensions are exemplary and not limiting. There can be provided a stylette, to fit within the cannula, of, for example, 21 gauge (for a 16 gauge cannula). The stylette can lock onto the distal end of the luer, at a luer lock hub. The stylette can remain in the outer needle as a user inserts the device near a disc (but not all the way to the disc), then be removed so as to allow the insertion of the longer inner needle, which can then penetrate into the disc, and can then, for example, be used to introduce therapeutics, for example, via a syringe.

FIG. 10 thus also shows, at the bottom of the figure, the second, or inner needle of the device. This inner needle fits inside the first needle/cannula, and protrudes from it into the disc. The inner needle can be, for example, 5 inches in length, where the bottom 20 mm or so have perforations out of which the therapeutic agents can diffuse into the patient. Such a device can have, for example, a cannula of 21-25 gauge. It can have a similar luer and finger grip, and can similarly accept a syringe which can lock on its luer lock hub, to deliver the therapeutics, as described above. There is no stylette for this inner needle, obviously.

FIG. 11 depicts a variant embodiment of the exemplary PIARES delivery device of FIG. 10, where instead of a luer lock hub at the proximal end of the inner needle, a septum is provided, thus completely isolating the delivery device and the disc into which the inner needle protrudes from exposure to the ambient space. To introduce therapeutic agents into the inner needle and thus out the distal holes into the disc, a user inserts a needle into the septum, in similar fashion as shown in FIG. 12 for the peripheral joint and spine embodiment of the delivery device.

Thus, in operation, a user first inserts the outer needle, with stylette inside. This is done under imaging guidance, such as, for example, fluoroscopy or ultrasound. The outer needle is placed near, but not all the way towards, the relevant disc. The stylette is then removed, and the inner needle inserted inside the outer needle. Thus, as shown, the outer needle can be 16 gauge, and the inner needle from 21 to 25 gauge, for example. Because it is longer than the outer needle, for example, 5 inches versus 3.5 inches, as shown in FIGS. 10-11, the inner needle protrudes out the end of the outer needle, and can be guided into the disc itself. Now at this point the distal end of the inner needle touches the disc, but if the septum embodiment of FIG. 11 is used on the inner needle, the system is completely closed. Once intradiscal, therapeutic can be introduced via the inner needle.

Thus, the PIARES device has a number of novel advantages: (i) it provides a fully and completely closed system when the septum is used on the inner needle's proximal end; (ii) therapeutic can be delivered simultaneously to the nucleus and annulus of the disc, thus to deliver therapeutic to where the tear is; and (iii) by using the outer needle for initial positioning, and then granularly positioning the longer inner needle, which is then fully set up to deliver therapeutic agents, trauma to the disc is minimized, as opposed to conventional approaches where needles are moved in and out. Less trauma means quicker healing and better disc repair.

FIG. 12 depicts detailed views of an exemplary delivery device according to an embodiment of the present invention directed to delivering therapeutics to bone-cartilage interfaces of peripheral joints and spine. It is a more detailed drawing of the exemplary device shown in exploded view at the top panel of FIG. 7, with a perspective view. As seen in FIG. 12, there can be a cutting tip, and proximally from it external screw threads between which are interspersed perforations. Thus the grip is first tapped with a hammer for initially setting it into place into dense cortical bone, and then subsequently twisted by a user to advance the delivery device into spongy bone (interior cancellous bone). The cannula can be from 14 to 16 gauge, for example, and at the proximal tip of the device there can be a needle pierceable septum seal, for example, or a luer lock with removable cap such that a syringe can be attached, as shown in various other embodiments and as described above.

While the shown version has a flat distal surface for tapping a hammer for the initial setting, in other exemplary embodiments an interface can be provided in the center of the end of the cap, to interface with commonly used drills, for example.

Illustrations of Delivery Device as Used in Knee Procedures

Figure 13:
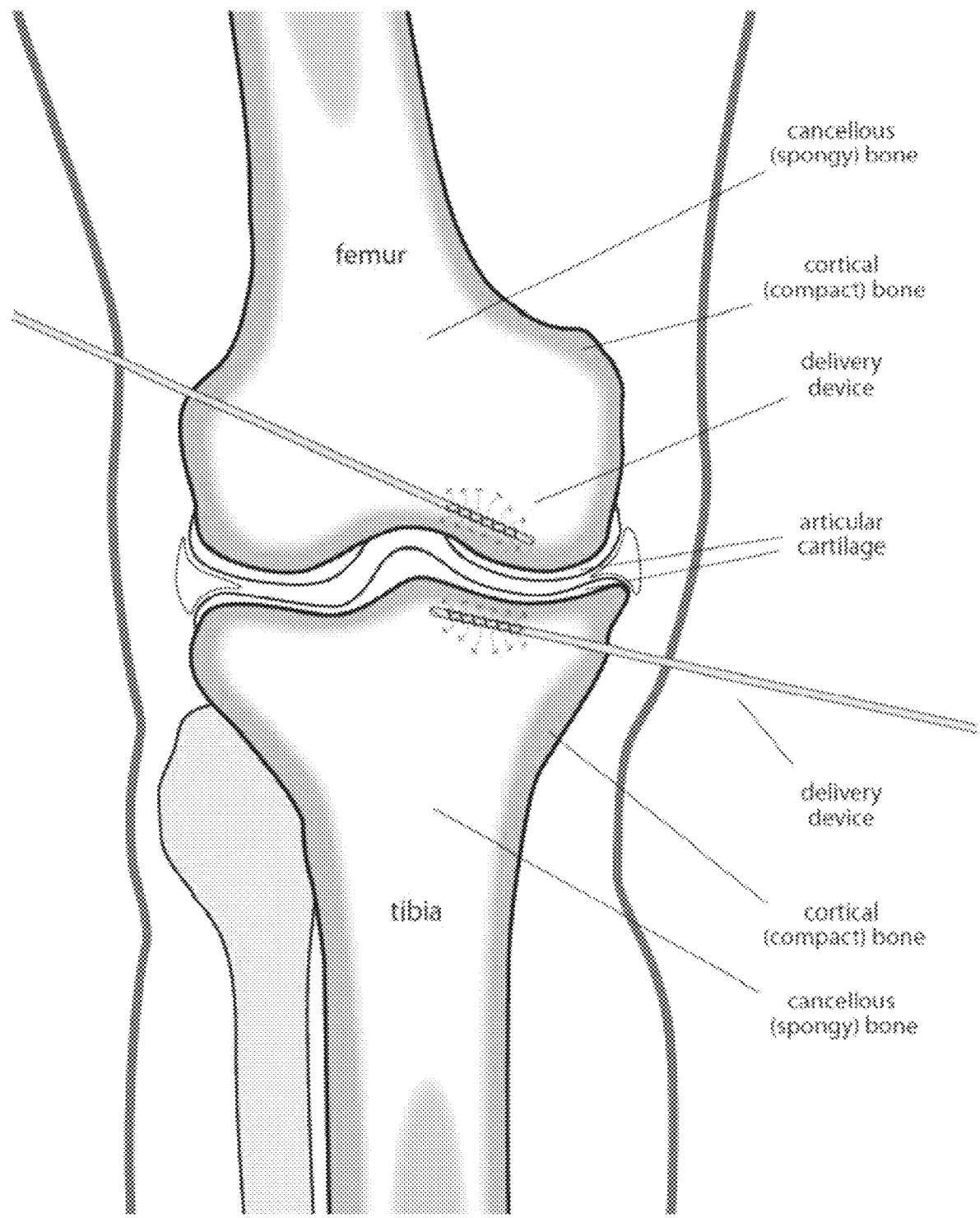
FIG. 13 depicts an exemplary delivery device being inserted into the bone above and below a right knee according to exemplary embodiments of the present invention.
Figure 14:
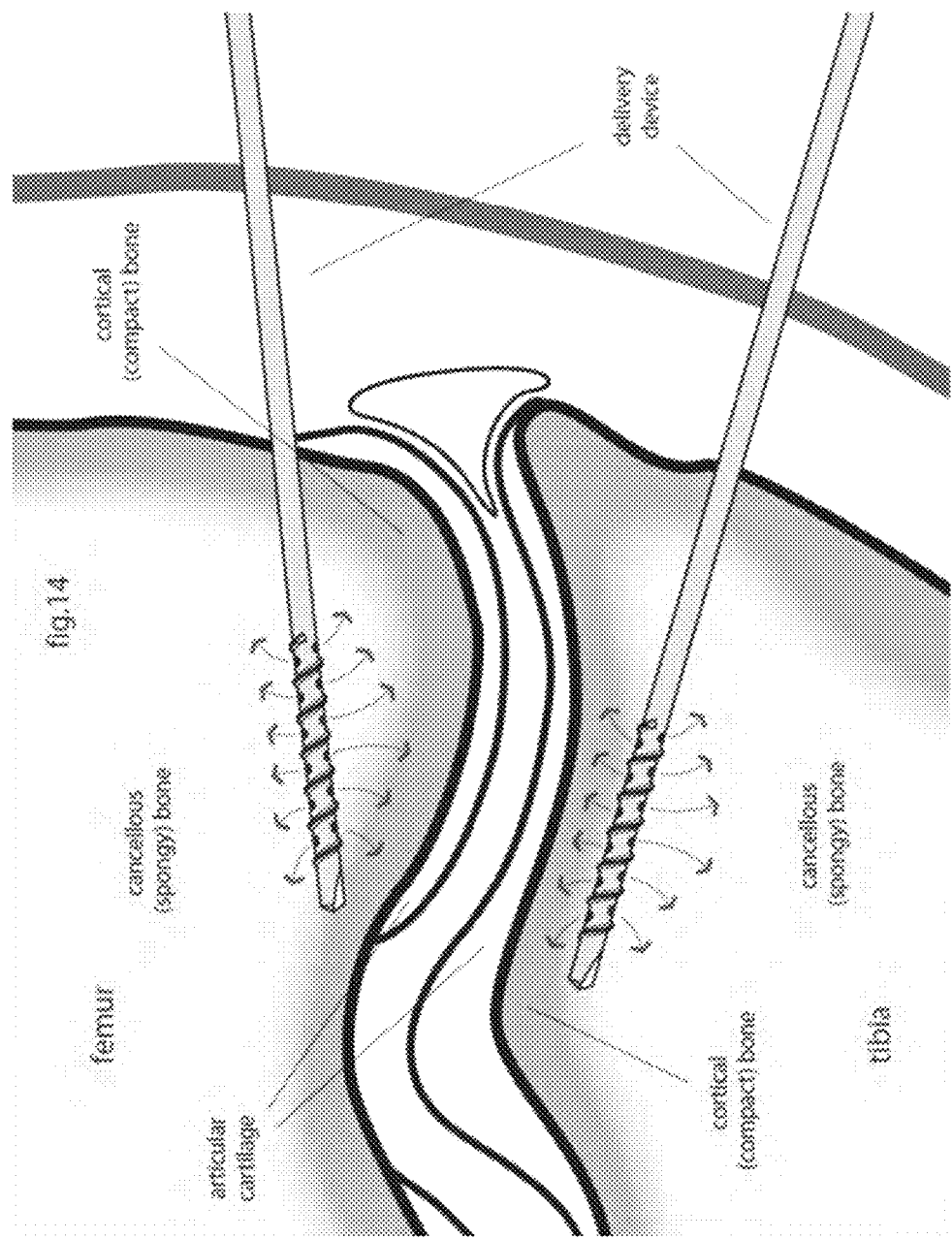
FIG. 14 depicts a magnified view of the knee joint, and adjacent tibia and femur from the drawing shown in FIG. 13.
Figure 15:
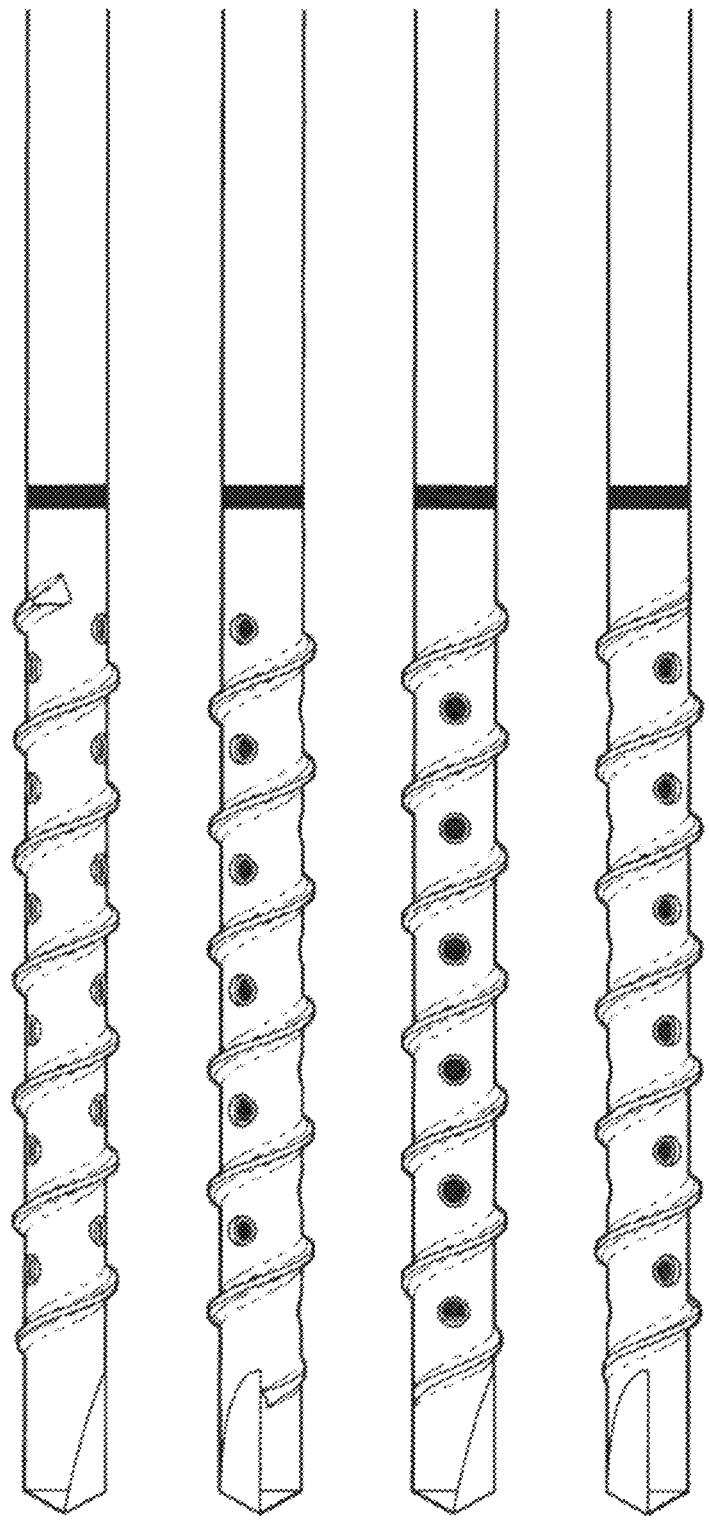
FIG. 15 depicts details of the distal portion of the exemplary delivery device of FIGS. 13-14.

FIGS. 13-15 illustrate exemplary use of the device of FIGS. 6-9 in knee procedures. FIG. 13 depicts an exemplary delivery device being inserted into the bone above and below an exemplary right knee according to exemplary embodiments of the present invention. Because this is a peripheral joint, the device of FIG. 12 would be used. As can be seen in FIG. 13, the device is generally inserted above and below the affected joint, and is inserted so as to be close to the interior edge of the cortical bone, above and below the cartilage of the affected joint. In the case of the knee joint depicted, one delivery device is inserted above and below the articular cartilage of the knee. As described above, using the protocol described above, the therapeutic introduced by the practitioner or user diffuses from the holes in the distal end of the cannula, and the bone marrow is stimulated by a GCSF to produce mesenchymal cells (MSC). As these cells come out of the bone marrow and make their way towards the BCI they get exposed to PRP before reaching the bone-cartilage interface. The exposure to PRP is believed to thus induce the MSCs to become cartilage.

FIG. 14 depicts a magnified view of the knee joint, and adjacent tibia and femur as shown in FIG. 13, further illustrating the diffusion of therapeutic(s) uniformly away from the cannula. FIG. 15 depicts details of the distal portion of the exemplary delivery device of FIGS. 13-14, showing the threads and the holes interspersed between them, at various rotational orientations of the delivery device.

Alternate Exemplary Delivery Device—"PecaBoo"

FIGS. 16A-21 are detailed design drawings of an alternate improved exemplary delivery device tool according to an exemplary embodiment of the present invention. Variations of this device ma, for example, be used in knee, hip and other joint procedures. This alternate delivery device is next described.

An exemplary prototype of the tool of FIGS. 16A-20 was fabricated, and tested on various patients with DJD of the knee with excellent results. The exemplary tool may be known and/or marketed under the trade name "PecaBoo."

Figures 16A, 16B, 16C:
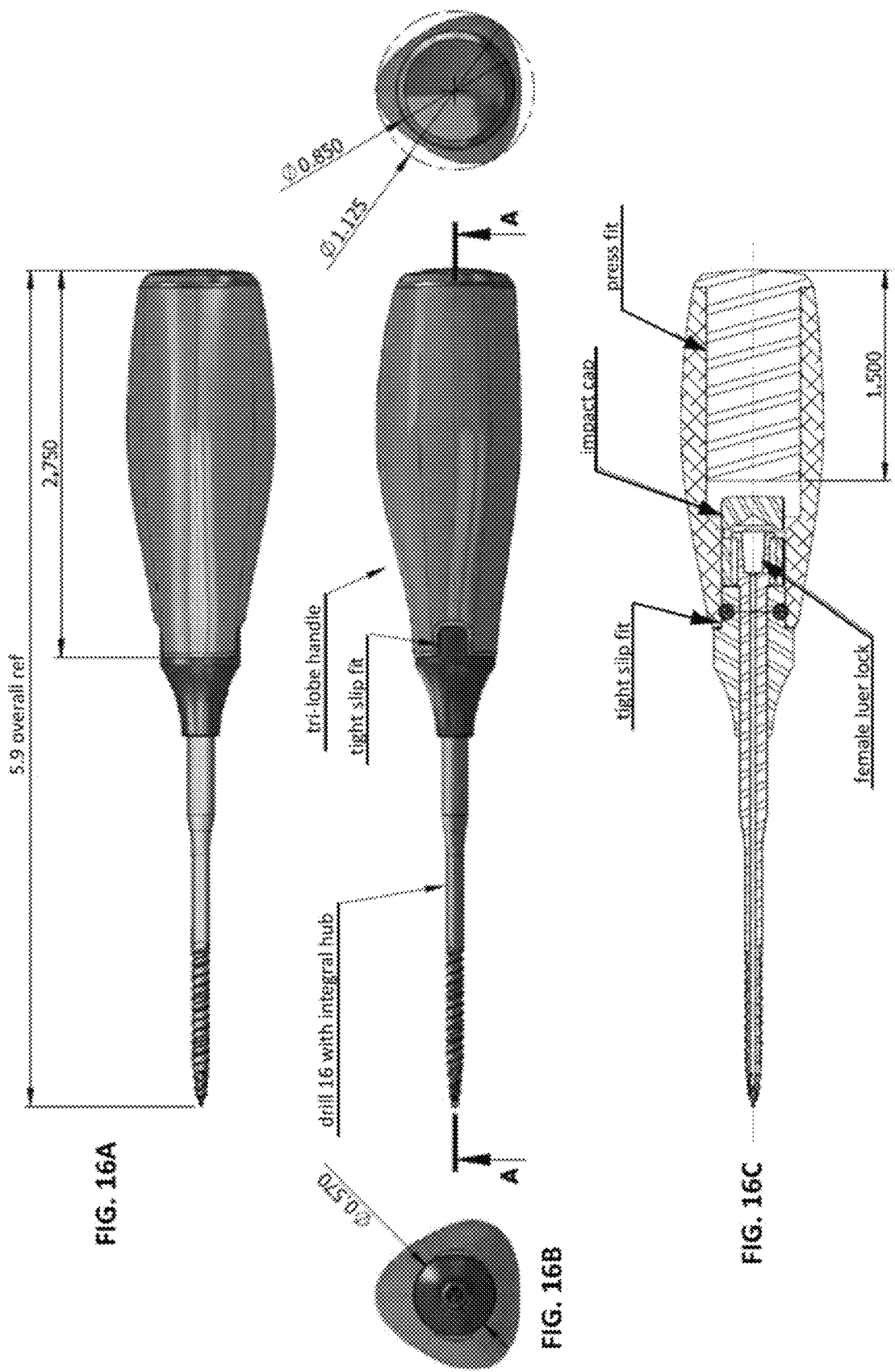
FIG. 16A depicts an overview an overview of an alternate exemplary "PecaBoo" delivery device according to exemplary embodiments.
FIG. 16B depicts a tri-lobe handle of the exemplary delivery device of FIG. 16A.
FIG. 16C depicts a longitudinal cross section of the exemplary delivery device of FIG. 16A.

FIGS. 16A-21D, next described, illustrate two versions of an exemplary delivery device according to exemplary embodiments of the present invention. With reference to FIG. 16A, this is an overall view of the device. The device has three primary parts: a drill portion, an impact cap and an ergonomic tri-lobe handle. The tri-lobe handle is shown with its top and bottom views, respectively, in FIG. 16B. As can be seen on the top of the tri-lobe handle there is a built in metal pad shown, for example, in FIG. 16C, at the far right image, which occupies almost all of the space of the top portion of the tri-lobe handle. This metal portion can be used once taken off the tool and turned around as a kind of a hammer, mallet or tapping device to push in the drill, when covered by the impact cap, into a patient's bone. The impact cap prevents damage to the hub in such a use. It is noted that the exemplary dimensions provided in FIGS. 16A-21D are exactly that, exemplary, and this is one of many prototypes that can be built according to various exemplary embodiments of the present invention. The dimensions are left for illustrative purposes only to provide exemplary aspect ratios, as well as exemplary dimensions, for a tool that has been found to be convenient to certain practitioners.

With reference to FIG. 16C, which is a longitudinal cross section of the exemplary tool, there is a tight slip fit between the tri-lobe handle and the drill portion of the tool, such that the handle tightly fits upon the tool such that it can be turned and manipulated. Also seen in the cross section is the impact cap which covers the luer at the proximal end of the drill as illustrated in more detail in the following figures. It is noted that in these figures the drill is referred to as "drill 16." The "16" refers to an internal design identifier.

With reference to FIGS. 17A-17D, there is seen the drill with integral hub at 17A, an O-ring which slips over the hub at 17B, the impact cap referred to above, at 17C and the tri-lobe handle at 17D. These fit together as shown, where the O-ring is slipped over the top of the drill with integral hub so that it sits as shown in FIG. 16C. This then creates the tight slip fit of the tri-lobe handle on the hub. Alternatively, C clip rings can be used instead of an O-ring—which would need to be replaced after some time—or, for example, other attachment mechanisms as may exist in the art. The impact cap shown in FIG. 17C covers a female luer lock such that the drill is totally closed and not exposed to the air any more than absolutely necessary. The impact cap allows the tri-lobe handle, as shown at 17D, to be removed from the remainder of the tool and still allow the tool to be a completely closed system. Moreover, a practitioner can, upon removing the tri-lobe handle as noted above, turn it around such that the metal place built into the top of it can be used to tab on the impact cab shown as FIG. 17C without damaging or affecting the rest of the tool, namely the drill with integral hub shown at FIG. 17A. In exemplary embodiments of the present invention the drill may be disposable and the handle reusable, or the entire device autoclavable and reusable.

Figures 18A, 18B, 18C:
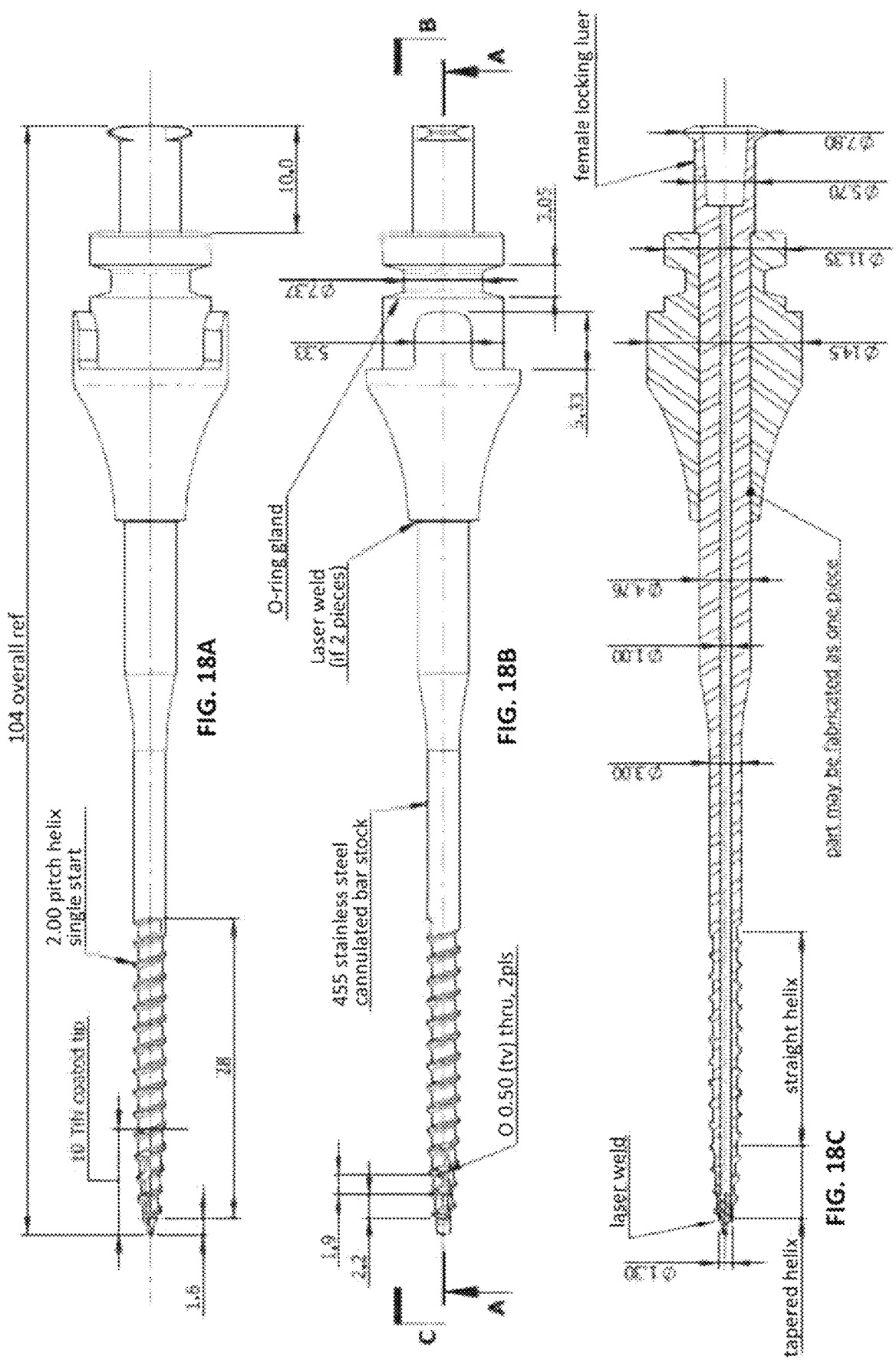
FIGS. 18A, 18B and 18C illustrate the exemplary delivery device of FIGS. 16A-16C and 17A-17D, in two longitudinal views and a longitudinal cross section, respectively.

FIGS. 18A-18F illustrate the exemplary delivery tool of FIGS. 16 and 17 in various longitudinal views and longitudinal cross section. With reference to FIG. 18A the female locking luer is shown at the far right as well as the integral hub upon which, for example, an O-ring (as shown at FIG. 17B) can be placed to provide a tight slip fit. Additionally, FIG. 18A shows, for example, a 2.0 pitch helix to the cutting threads and illustrates further that the tip of the drill can be coated with a coating such as, for example, titanium nitride, or TiN. TiN is an extremely hard ceramic material which is often used as a coating on titanium allows, steel, carbide and aluminum components to improve the substrate surface properties. Because of these hardening properties, such a coating can be used to protect cutting and sliding surfaces of medical devices, and it is also used as a non-toxic exterior for medical implants, making it ideal to improve the hardness and cutting ability of the tip of the exemplary delivery tool and at the same time be medically inured to the patient's tissues. As before, exemplary dimensions are provided in FIG. 18, and they are, of course, simply illustrative and not intended to bind or limit the invention in any way. FIG. 18B illustrates the O-ring gland, and an exemplary laser weld if the drill and hub are decided to be made in two pieces. Alternatively, they can be made in one piece and machined. FIG. 18B also illustrates how the drill can be made of 455 stainless steel cannulated bar stock, for example. Other metals and stainless steel grades are also usable, in various exemplary embodiments.

FIG. 18C, the longitudinal cross section, again shows exemplary diameters, which are only illustrative. This figure also illustrates that the drill with integrated hub can be fabricated as one piece and that the tip of the drill has a straight portion, as well as a tapered portion occupying the most distal portion of the delivery device, to make it more easily insertable into a patient. There are also seen in the depictions of FIG. 18 at the tip of the device some grooves slightly distal to the actual tip which are shown in greater detail in FIGS. 19A through 19C. Finally, the tip can be laser welded to the cannulated drill portion, as shown in FIG. 18C.

FIGS. 18D through 18F are copies of FIGS. 18A through 18C, respectively, somewhat magnified, with further explanatory notes by the present inventors. With reference to FIG. 18D one can see that there are perforations in the distal tip of the exemplary delivery device, as called out by the inventor notes. These perforations are the holes by which the fluid is delivered. In a variation from that shown in the device of FIGS. 13 and 14, in this exemplary embodiment there are only a few holes. Actually two full perforations across the entire diameter of the distal tip of the exemplary device, making four holes in total, located only at the most distal portion. Of course, they have to be proximal to the point at which the spade-type cutting tip, as shown in FIGS. 18E and 18F, but they can be immediately proximal of that as shown in FIG. 18F. It is found that a smaller number of holes placed at the extreme distal portion of the exemplary tool or delivery device allow the therapeutics to be delivered closest to the bone chondral interface. Thus, once a practitioner has screwed in the device as far as he needs it to be (and this is done under fluoroscopy as described above, and as shown in the photographs of actual procedures described below) he or she can then unscrew the device slightly, moving it back, and dispense the medication into the cavity created at the tip of the device by slightly moving back the device or unscrewing the device. The physician can, for example, unscrew slightly and deliver medication, and repeat this process a few times, and thereby fill up a section of the channel created. This ensures that the medication goes to where it is most useful, and does not leak out the back of the device.

Also shown in FIG. 18D there are thread cutting flutes which are shown in a magnified depiction immediately beneath FIG. 18D. These are, as described above, used to cut the bone as the drill is turned by a user as it is protruding into the patient's bone. Additionally, one can see the taper of the distal tip as shown in the drawing below FIG. 18D, and the fact that the tip itself can be laser welded all around to make sure that it is well fastened within the cannula. FIG. 18E also depicts an exemplary internal thread diameter—or minor diameter—of the threaded portion of the tool, as well as the external thread diameter—also known as the major diameter. The tapered thread portion of the distal portion of the tip is illustrated in FIG. 18E.

Finally, FIGS. 18D and 18E illustrate the engagement key by which the hub may be attached to the handle, and further depict the threaded luer lock engagement by which that occurs. Moreover, in FIG. 18F the various portions proceeding from the proximal to the distal end of the exemplary drill are shown, from right to left, beginning with the female luer, the hub, the cannulated shaft, the center lumen, the threads, and the "spade" type cutting tip. The attachment of the hub to the cannulated shaft, if it is two pieces, can be by welding all around or in two places, or, for example, the combination of hub and drill, i.e. the cannulated shaft, can be fabricated as one piece and formed by machining.

FIGS. 19A through 19C illustrate an overall exemplary dimensional relationship between the drill with integrated hub and the threaded distal portion thereof. For example, the threads can occupy approximately 30% of the overall length of the drill with integrated hub in one example. Again, as noted above, these dimensions are purely illustrative and various other dimensions and dimensional relationships can be implemented in various exemplary embodiments of the present invention, all within the scope of the present invention.

FIG. 19A illustrates the drill with integrated hub without the impact cab and without the handle. Within FIG. 19A, a section of the tip is labeled as "D" and that is presented in FIG. 19B in a greatly magnified view. This tip contains both the fluid side ports by means of which therapeutics and/or liquids are dispensed into a patient using the exemplary delivery device, as well as various cutting features. There is a spade drill point which has essentially a flat surface on two sides and cutting edges at the tip. This makes for much easier cutting than a fully cylindrical shape. Once the spade point is inserted, when the user turns it creates a cylindrical bore. As can be understood, the exemplary delivery device of FIGS. 16A-19C is, as noted, capable of being slightly pounded or tapped into the bone of a patient above and below, for example, the knee joint or above and below, for example, a hip joint. As opposed a simply non-tapered cylinder, it is much easier to penetrate the bone and then cut the bone as the device is turned. This easily creates a pathway for the drill to proceed through the bone to a point close the bone chondral interface. Therefore the combination of (i) the spade drill point, (ii) the thread cutting flutes, and (iii) the tapering of the drill tip, all in combination allow for easy cutting of the bone surrounding the tip as a practitioner turns the drill such as, for example, by holding the tri-lobe handle shown in FIG. 17D, or, if she has sufficient strength, by simply twisting the integral hub or the impact cap. In alternate exemplary embodiments some or all of these features can be provided, but it need not always be necessary to have all of them.

Figure 20:
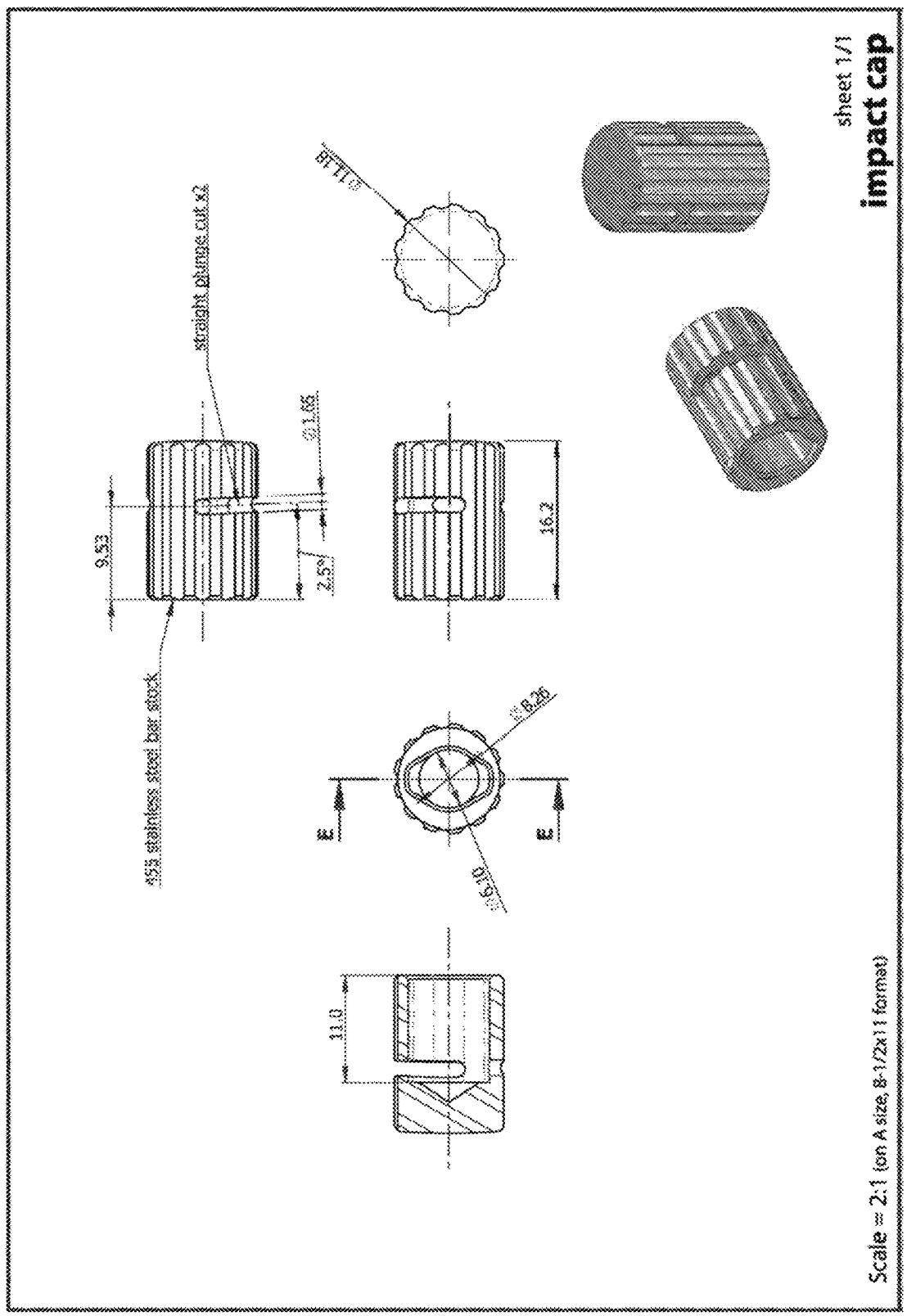
FIG. 20 illustrates exemplary details of an impact cap.
Figure 21:
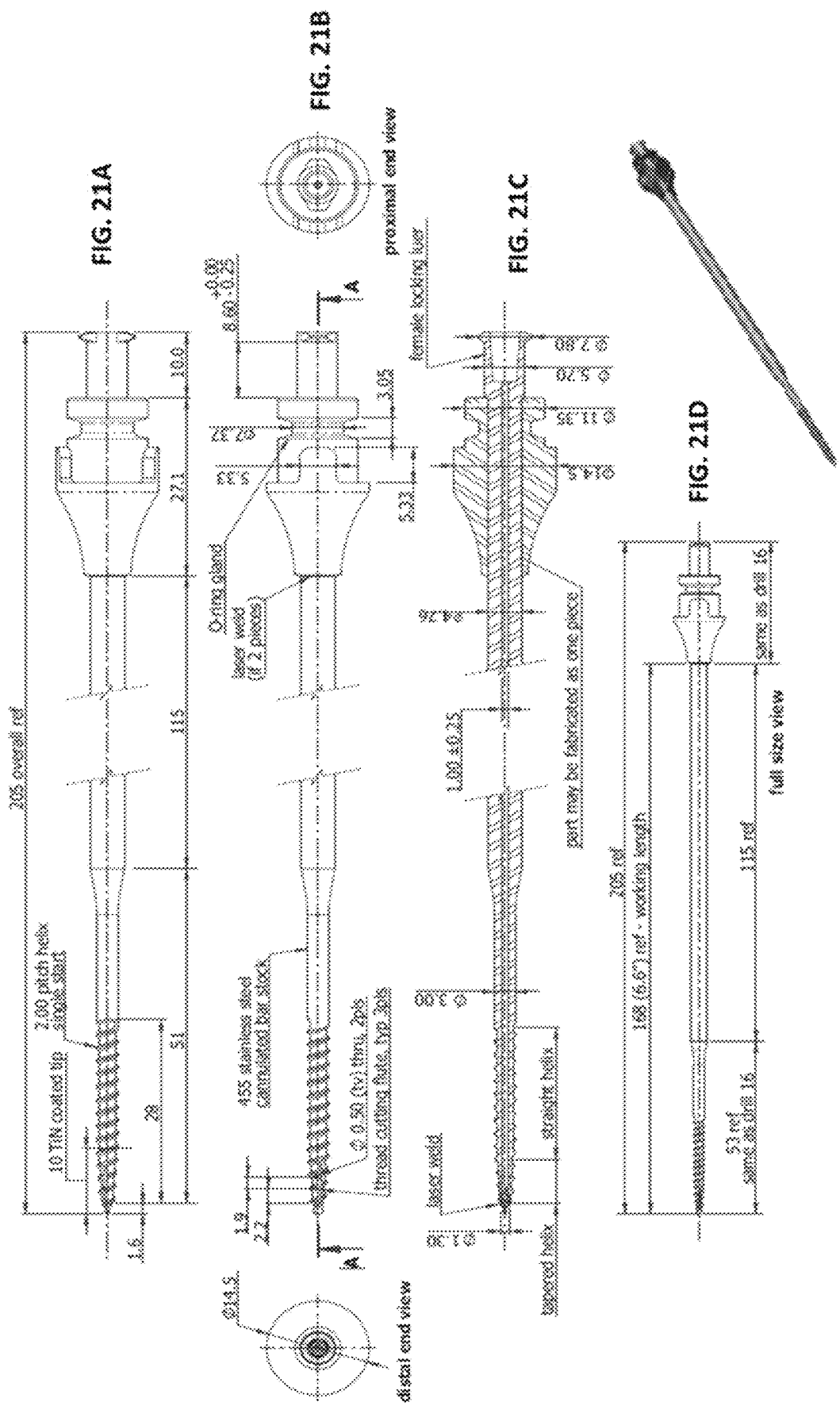
FIGS. 21A through 21D depict an elongated form of the exemplary PecaBoo device of FIGS. 16-20, such as may be used for hip procedures.

Along those lines, FIG. 20 illustrates exemplary details of the impact cap. As can be seen, it can be made of 455 stainless steel bar stock, it can have a straight plunge cut so as to be able to be fastened on the female locking luer as shown in FIG. 18 as well as in FIG. 17A, and it can have exemplary dimensions as shown, for example, or various other dimensions—the ones shown being completely exemplary and illustrative.

It is noted that the exemplary delivery tool of FIGS. 16A-20 has been found useful in treatment of weakened knee joints. As can further be well understood, for treating the hip joint, the same therapies described above can be used; however, to deliver the medicines, namely the PRP, the bone wax or calcium chloride and stem cells, if used, a slightly longer drill would need to be created to penetrate through the fat and muscle to get to the hip joint. Therefore, FIGS. 21A through 21D illustrate an elongated version of the exemplary drill with integral hub as shown in FIG. 18C for example. As can be seen with reference to FIG. 19A (top image), the overall length of the exemplary knee drill delivery tool is 104 mm, but in the case of the exemplary hip embodiment shown in FIG. 21D, the overall length is 205 mm, for example. Other relative dimensions are well within the scope of the present invention, it being generally understood that for most patients it takes a somewhat longer device to reach the hip than it does to reach the knee joint.

Other exemplary dimensions of the hip-type drill, are shown in FIGS. 21A, 21B, 21C and 21D. The device is essentially the same or similar to the exemplary knee version of FIG. 18, except for the length of the drill itself, and in particular the length of the portion proceeding the tapers that is not threaded. The threaded portion, as shown in FIG. 21D, can be, for example, the same as "Drill 16" which is the project name for the exemplary knee delivery tool shown in FIGS. 16A-20. ("Drill 17" being the project name for the exemplary drill for hip joints).

FIGS. 22A and 22B are drawings of the exemplary hip delivery device, namely the "Drill 17" device super imposed on a coronal section of a human left hip joint and showing surrounding muscles and tissues. The numbers referred to in FIGS. 22A and 22B are provided in the following Table for background and ease of locating where the exemplary drill is to be placed in exemplary embodiments of the present invention. As can be seen in the drawing, although this would not be done in practice, for ease of illustration, there is one drill shown in the proper position for the superior portion of the joint and one for the inferior portion of the joint, although obviously in practice these would generally be done sequentially and not at the same time.

Figure 22:
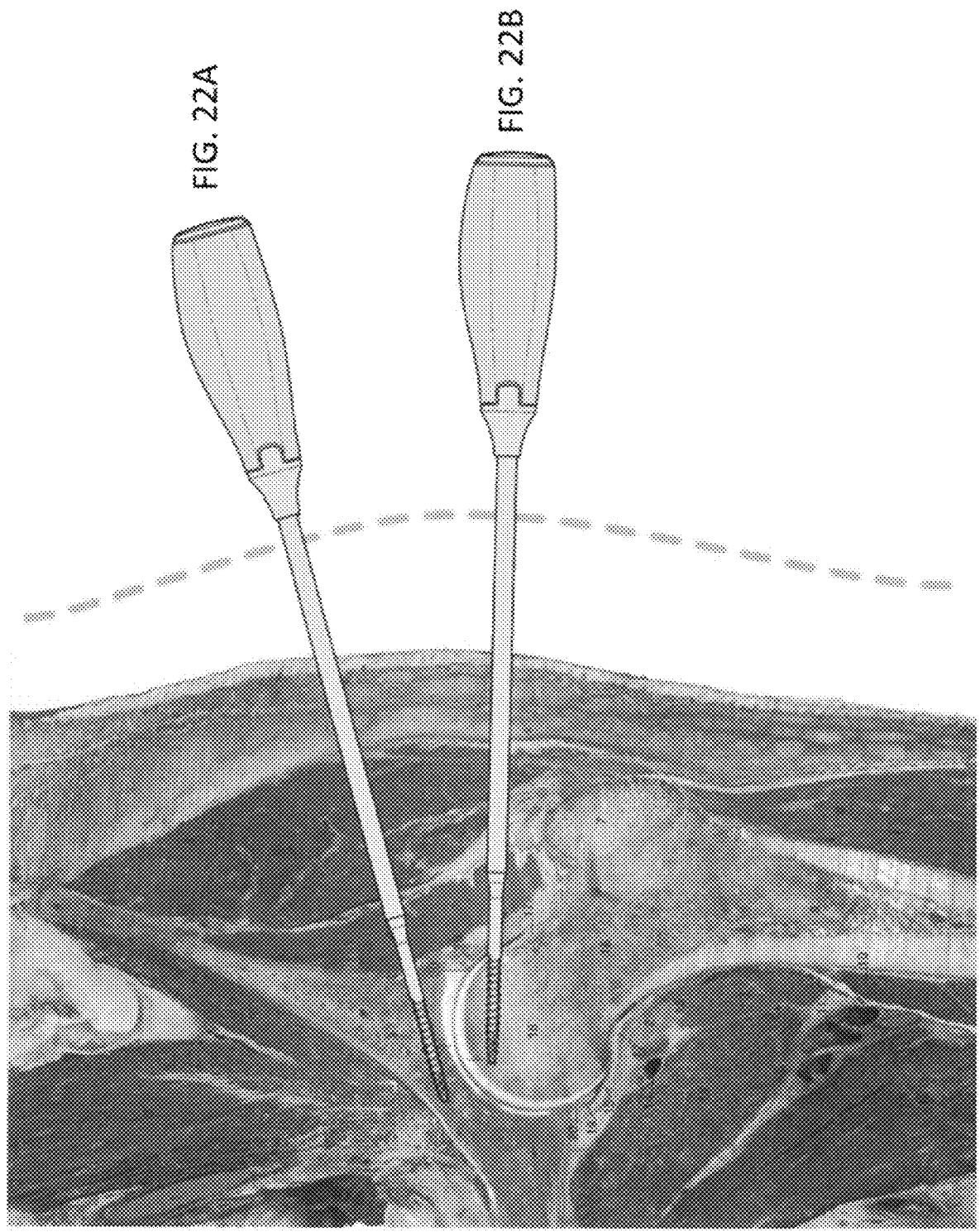
FIGS. 22A and 22B illustrate the exemplary PecaBoo device (hip length) as inserted into the superior and inferior compartments adjacent to an exemplary hip joint.

Table of Anatomical Areas for FIG. 22
1. External iliac artery
2. Psoas major
3. Iliacus
4. Iliac crest
5. Gluteus medius
6. Gluteus minimus
7. Greater trochanter
8. Vastus lateralis
9. Shaft of femur
10. Vastus medialis
11. Profunda femoris vessels
12. Adductor longus
13. Pectineus
14. Medial circumflex femoral vessels
15. Capsule of hip joint
16. Neck of femur
17. Zona orbicularis of capsule
18. Head of femur
19. Acetabular labrum
20. Rim of acetabulum
21. Hyaline cartilage of head
22. Hyaline cartilage of acetabulum Exemplary Clinical Use of PecaBoo Device Next described are FIGS. 23-48, which are photographs of exemplary actual procedures on human knees performed using the exemplary PecaBoo device described above. Procedures were done under fluoroscopic guidance, as noted above, and therefore both photographs of the patient's knees as well as some of the images from the fluoroscopy will be provided.

Figure 23:
FIGS. 23-48 depict an exemplary prototype of the PecaBoo tool shown in FIGS. 16-20 as used on a patient in an exemplary procedure on the knee, with corresponding high quality X-Ray images of various stages of the exemplary procedure.
Figure 24:

With reference thereto, FIG. 23 shows a practitioner initially inserting the PecaBoo device into a patient's knee close to the BCI, as described above. Similarly, FIG. 24 shows the same patient where the practitioner has pushed the device significantly into the patient and is obviously inserting into the bone.

Figure 25:
Figure 26:
Figure 27:
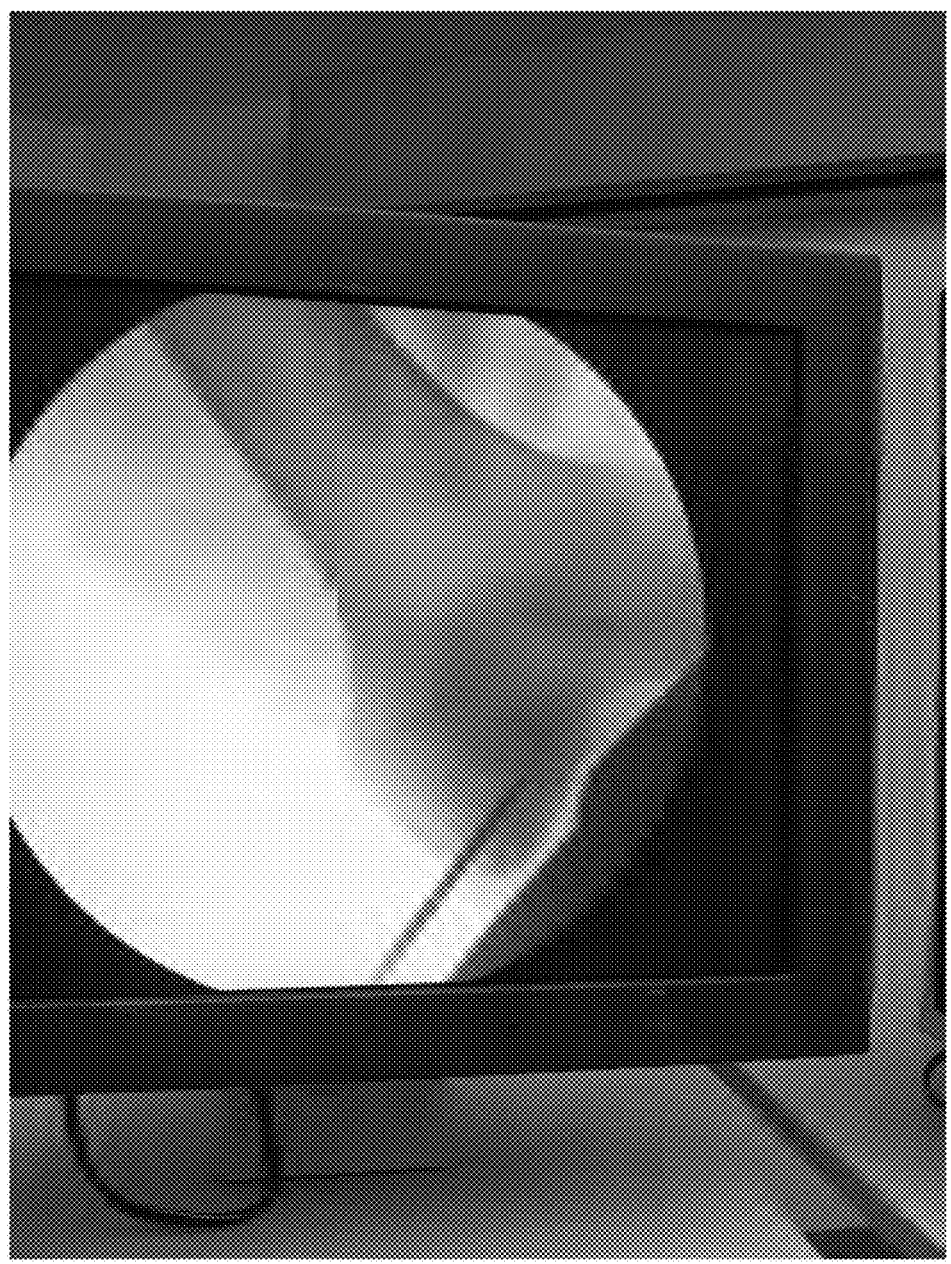
Figure 28:
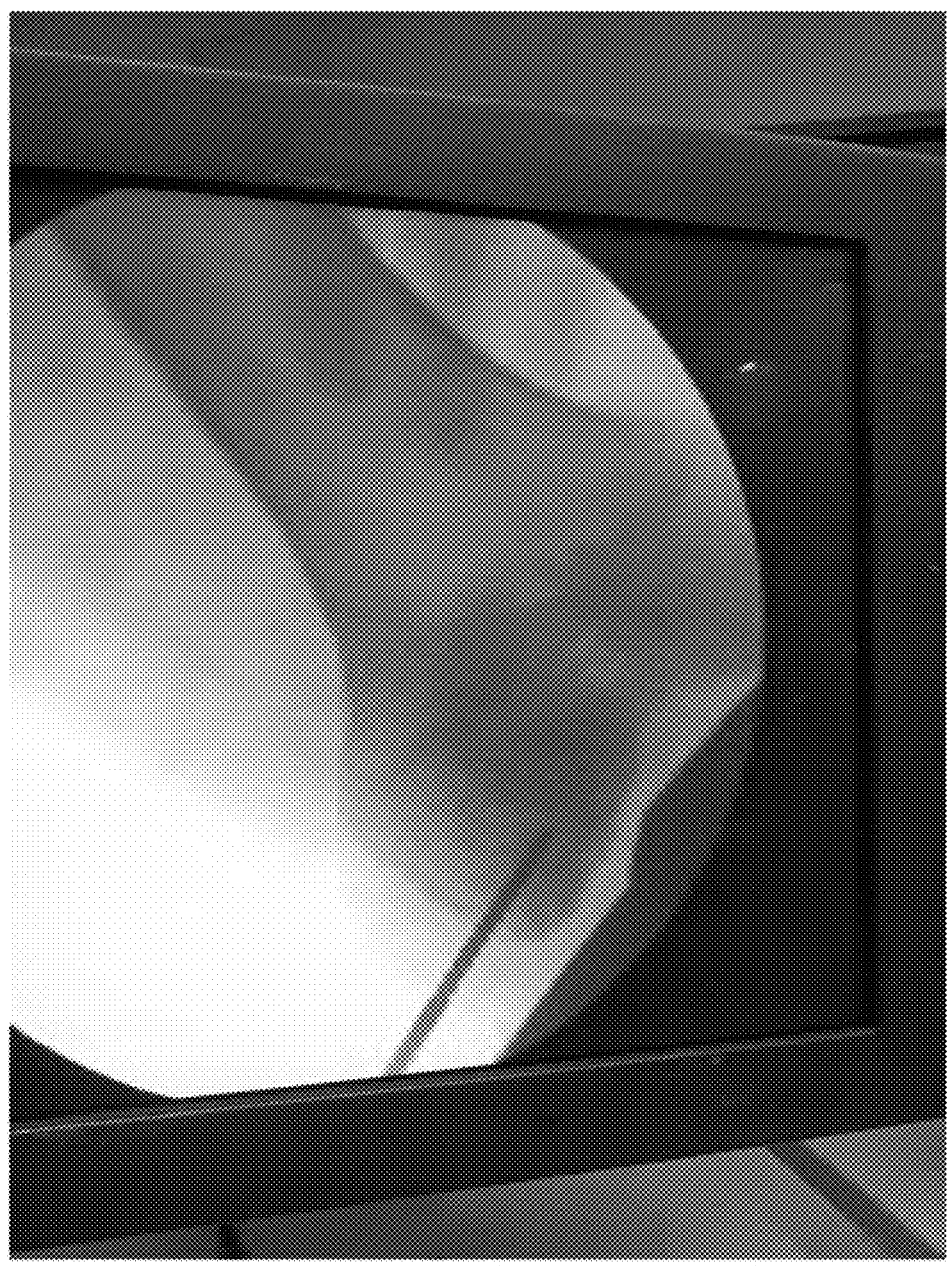

FIG. 25 shows an even further protrusion of the device into the bone and that is its stopping place as shown in FIG. 26. FIG. 27 shows that the exemplary PecaBoo device has been screwed into the bone near the BCI below the knee joint itself. FIG. 28 is a close up of the image shown in FIG. 27 showing the same thing.

Figure 29:
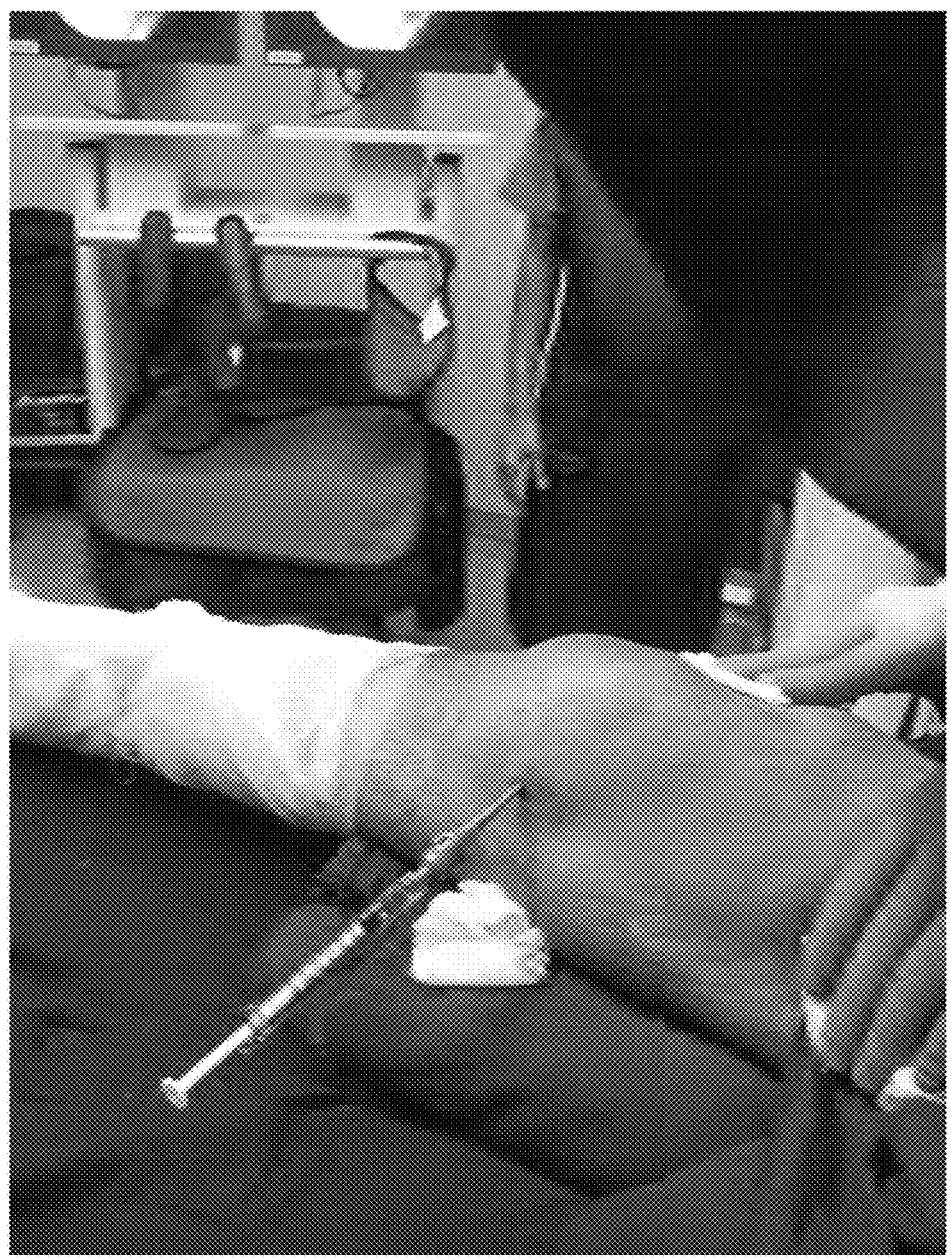
Figure 30:
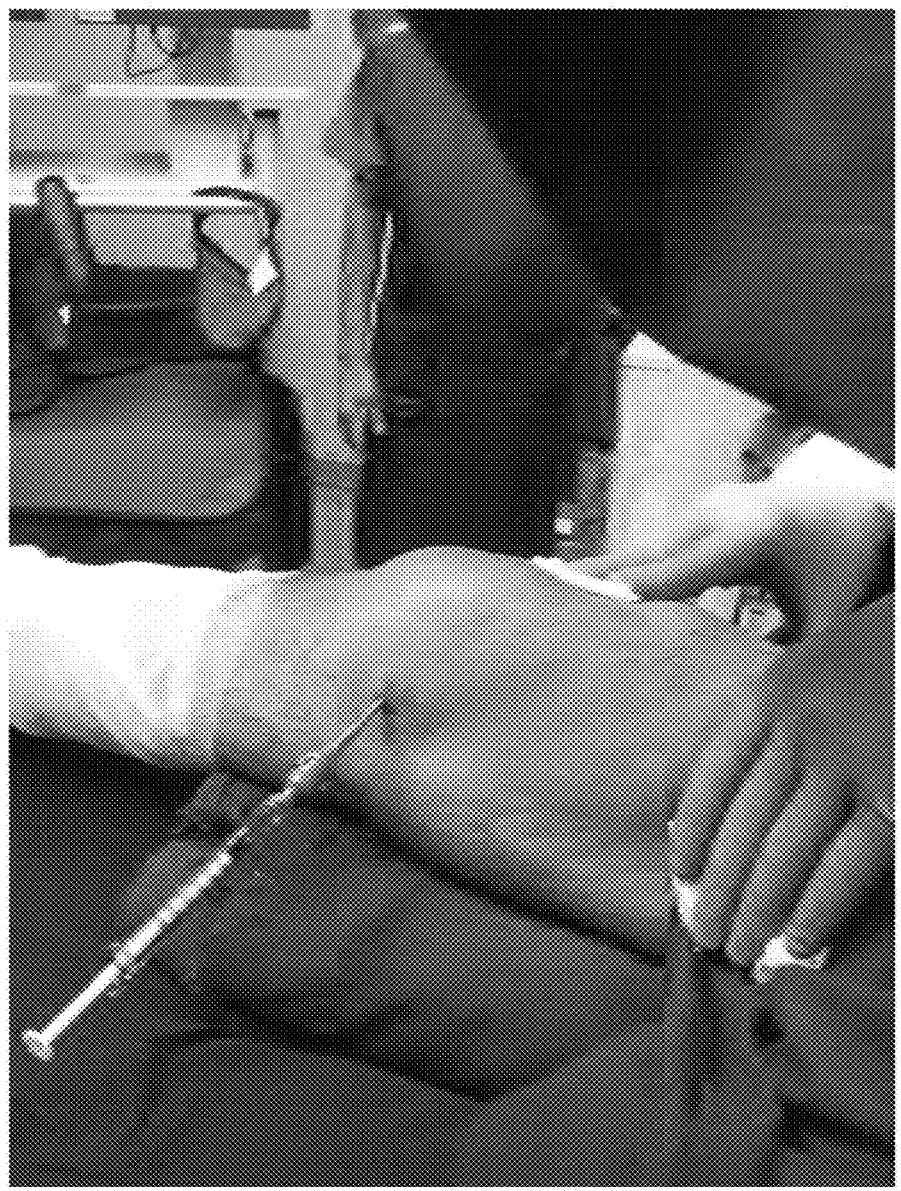

As noted above, after the device has been inserted into the bone near the BCI, the practitioner may, for example, remove the handle, remove the impact cap, and attach a syringe to the female luer which protrudes from the exposed portion of the hub after the impact cab has been removed. This is shown in FIG. 29. Additionally seen in FIG. 29 is the red ring of the exemplary O-ring remaining on the hub as shown in the expanded view of FIG. 17, except here in FIG. 29 the O-ring is placed securely onto the hub which allows the tight fit of the yellow tri-lobe handle seen in FIGS. 23 and 26. In the configuration of FIG. 29, the set-up is ready for injection as per one of the above described protocols. FIG. 30 shows a close up of the view of FIG. 29.

Figure 31:
Figure 32:
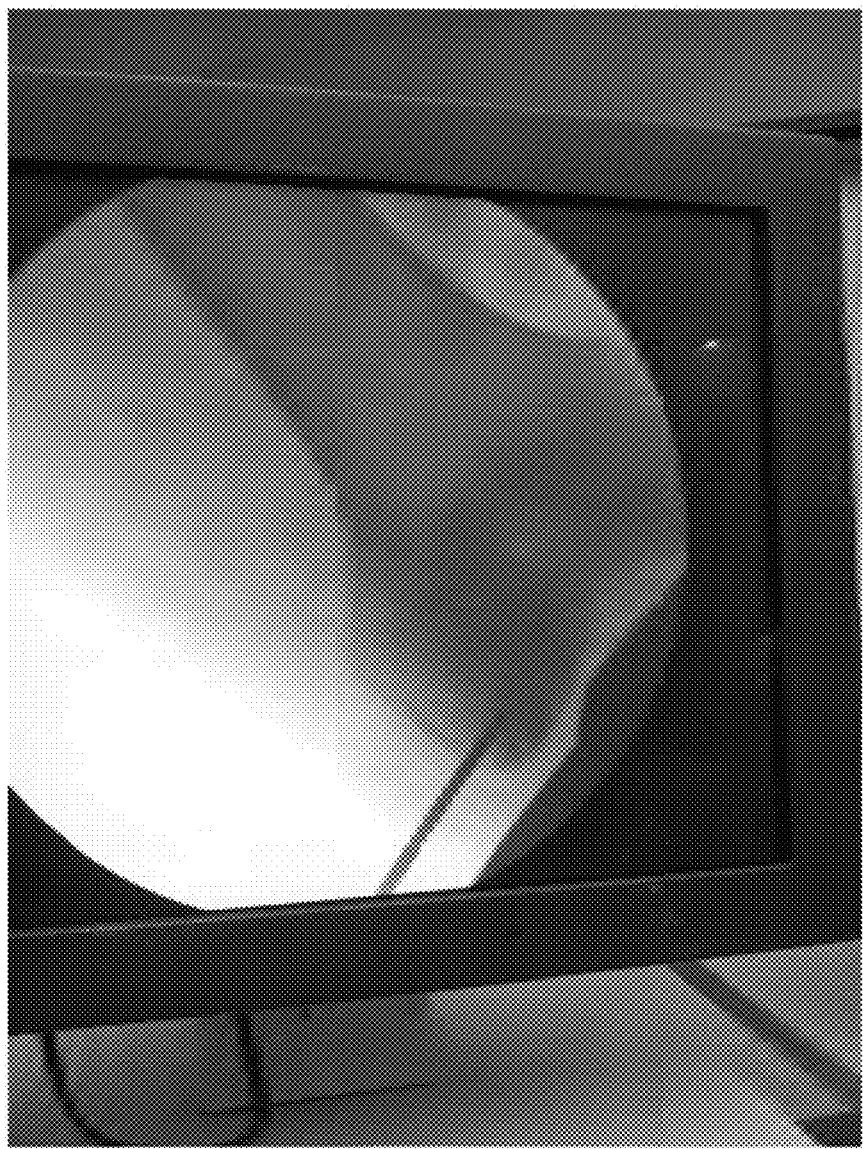

FIG. 31 now shows the syringe, which had been attached in the views of FIGS. 29 and 30, being removed. As noted above, when a practitioner injects the medication into the patient in the set-up of FIGS. 29 and 30, he or she will often back out the exemplary PecaBoo delivery device so that the medication can be injected into the cavity left behind. This backing up and injecting may, for example, be repeated numerous times. Therefore, at the end of an injection, the exemplary delivery device will protrude less into the bone than it did at the beginning of the injection. This is shown in FIG. 32 which shows the position of the protrusion of the device as shown in FIG. 31 into the bone which is less of a protrusion than that shown in FIGS. 27 and 29, after the initial screwing in of the delivery tool, as can readily be seen by comparison.

Figure 33:

FIG. 33 shows a view from the other end of the patient, i.e., looking upwards from the area of the patient's foot. This is a different patient than shown in the previous figures. As seen in FIG. 33, the practitioner has just begun inserting an exemplary delivery device near the patient's knee joint in similar fashion as shown above. In this case, however, the exemplary delivery device is being inserted superior to the patient's knee on the femoral side.

Figure 34:
Figure 35:
Figure 36:

FIG. 34 shows a little bit of advance of the device and FIG. 35 shows it having been pushed in all the way such that the therapeutics can now be delivered after removal of the tri-lobe handle and the impact cap. This situation is seen in FIG. 36, where syringes are being attached to the female luer of the device.

Figure 37:
Figure 38:
Figure 39:

FIG. 37 shows the protrusion of the exemplary device into the affected area on the femoral side of the joint. It is also noted in FIG. 37 that the patient has already had bone screw and other hardware inserted from prior procedures.

Figure 40:
Figure 41:
Figure 42:
Figure 43:
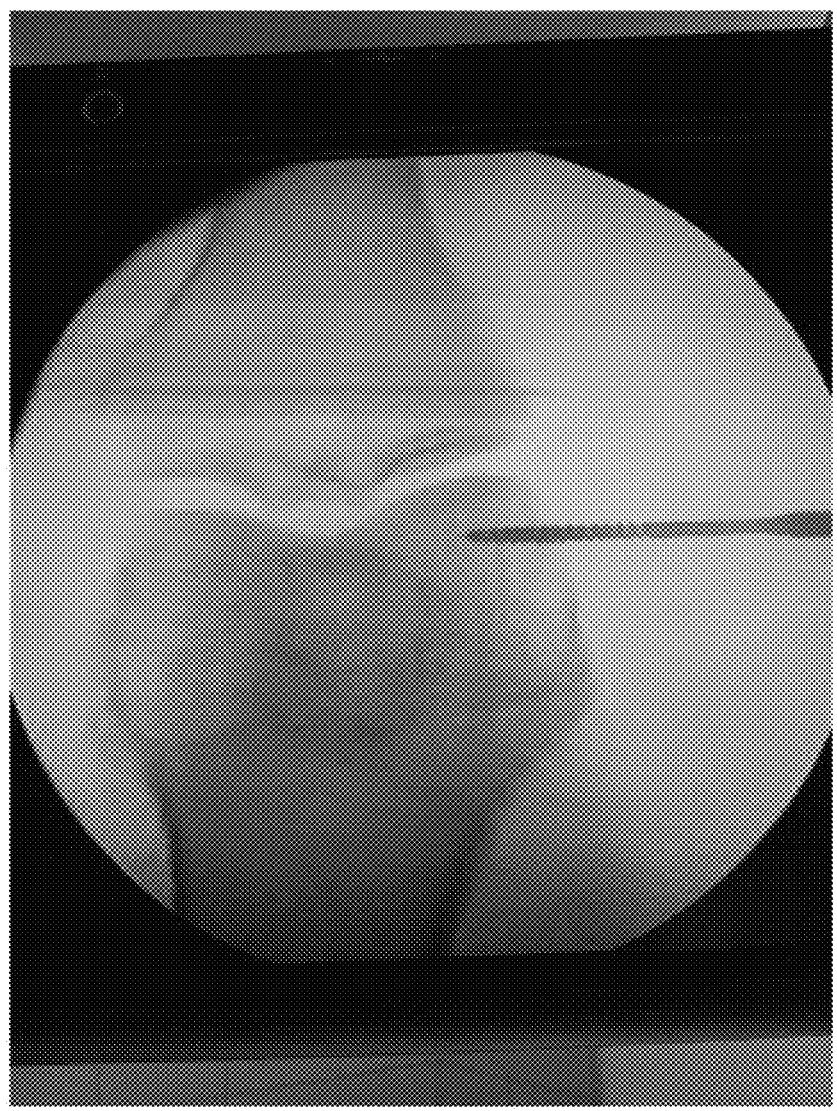

FIG. 38 shows once again the device being inserted into the knee of a patient as described before, and FIG. 39 shows it having been protruded quite some distance into the patient's body which was necessary given the patient's tissue width. FIG. 40 shows the device under fluoroscopy into the bone superior to the knee joint corresponding with the view of FIG. 39. FIG. 41 shows the same patient now being made ready for the injection, and FIG. 42 shows the injection using a syringe inserted into the female lure of the exemplary device. FIG. 43 is another image obtained from the fluoroscopic guidance as the practitioner was performing the injection.

Figure 44:
Figure 45:
Figure 46:

FIG. 44 depicts another view of similar to that of FIG. 42 but from a different angle showing the device with the hub shown. FIG. 45 illustrates an injection into that same patient as does FIG. 46 when the injection has essentially been completed.

Figure 47:
Figure 48:

FIG. 47 shows the beginning of an exemplary procedure where the device is first inserted into a patient, and FIG. 48 shows the fluoroscopic guidance where the distal tip of the drill is just penetrating the position inferior to the knee joint on the top of the tibia.

It will be understood that the images of FIGS. 23-48 are merely exemplary and illustrate one example of the use of an exemplary delivery device according to the present invention with regard to patients with degenerated cartilage, or for example, edema resulting from an ischemia, in the knee joint.

Thus, in exemplary embodiments of the present invention, for joints, such as, the knee, for example, there may be female luer locks to minimize air exposure. For PIARES, for example, the intradiscal system, the same system may be used. Alternatively, in each case—PIARES, PecaBoo or the device of FIGS. 6-9, in some exemplary embodiments there can be either a fully closed system, using a septum, or, for example, one with female and male luer locks, minimizing air exposure.

Thus, in some embodiments a knee device, such as PecaBoo, may have female and male luer locks, and PIARES for intradiscal use may have a septum and be a fully closed system. In others all of PIARES, PecaBoo and other systems may be totally closed and use septums or the like.

Kits may be provided with each type, or with one type, either closed system or male and female luer locks, or a given kit may mix and match. Exemplary delivery devices may also be sold separately.

As noted above, in exemplary embodiments of the present invention, the drill and hub, as shown in FIGS. 18A through 18C, for example, may be preferably fabricated in one piece without seams, but may also be provided in two pieces, as shown, with two pieces with a continuous 360 degree welded seam fully sealing around where the drill passes through the hub. One piece is often preferred for reasons of cost as well. It is noted that even when fabricated in one piece, in some exemplary embodiments the hardened tip may still need to be made separately and welded onto the distal end drill, as noted above.

Thus, in exemplary embodiments of the present invention, a surgical hand tool can be provided, used for the non-invasive placement and delivery of therapeutics, to a targeted site. This can be done through minimally invasive skin incision, or without any incision, as may be desired. The delivery and placement of the therapeutic can be controlled and does not need a powered drill or guide wire.

An exemplary device can have a closed pointed end, a threaded portion, and be provided with thread cutting/forming features, such as flute(s), and can have a shaft perforations to the central lumen at a distal end to deliver therapeutics or other preparations. At the proximal end, means can be provided to attach a syringe in communication with the shaft's central lumen, and there may be a keyed engagement feature for attachment of a hand grip. The delivery device can be made of sufficient length to reach bone on either side of a desired or targeted joint, and to easily penetrate soft tissue and cortical bone to reach a targeted site in cancellous bone adjacent to a cartilage defect.

The device's main shaft or drill portion can be made of hardened stainless steel, or the like, such as, for example, 400 series or 17-40 stainless steel, for example.

The device can have, for example, an attachable/removable hand grip for ease of placement of the drill bit to a site, with a solid proximal end with which to tap or hammer, and with a grip for torquing the device through cortical bone and to guide a threaded shaft to a targeted site in cancellous bone, for example. The grip can have an ergonomic form for ease of use, such as a tri-lobe handle, which mimics the natural turn of a wrist in 120 degree increments.

The device can have an impact cap to (i) provide impact anvil surface to protect a proximal luer during impaction, as well as to (ii) close the luer opening to a shaft lumen.

The above-presented description and figures are intended by way of example only, and are not intended to limit the present invention in any way except as set forth in the following claims. It is particularly noted that persons skilled in the art can readily combine various technical aspects of the elements of the various exemplary embodiments described above in numerous other ways, all of which are considered to be within the scope of the invention.

The invention claimed is:

1. A method for treating osteoarthritic disorders, said method comprising:
    identifying an area of osteoarthritis of articular cartilage in a peripheral joint that comprises a first bone and a second bone;
    creating within said first bone a pathway to a bone-cartilage interface associated with said area of osteoarthritis; and
    delivering a bone-cartilage interface therapeutic material, through said pathway, sufficiently close to said bone-cartilage interface so that said method is effective to relieve pain,
    wherein said method comprises advancing a delivery device to a location within said first bone such that a distal end of said delivery device is located close to or at said bone-cartilage interface of said articular cartilage in said area of osteoarthritis, and wherein said delivering said bone-cartilage interface therapeutic material comprises delivering said bone-cartilage interface therapeutic material through said delivery device.

2. The method of claim 1, further comprising performing said identifying step, said creating step, and said delivering said bone-cartilage interface therapeutic material step on said second bone.

3. The method of claim 1, wherein said bone-cartilage interface therapeutic material is selected from the group consisting of: platelet-rich plasma; growth factors from platelet-rich plasma; granulocyte colony-stimulating factors; bone marrow aspirate; stem cells; adipose tissue derived stem cells; culture expanded autologous stem cells; autologous embryonic stem cells from cord; embryonic stem cells from a cell bank; very small embryonic like cells; hyaluronic acid; a drug; and a biologic.

4. The method of claim 1, further comprising delivering a clot-forming substance into said first bone.

5. The method of claim 4, wherein said clot-forming substance is selected from the group consisting of: a calcium chloride solution; and thrombin.

6. The method of claim 1, wherein said peripheral joint is a knee or a hip.

7. The method of claim 1, wherein said peripheral joint is a knee, and wherein said bone-cartilage interface therapeutic material is delivered into a femoral medial compartment or a femoral lateral compartment or into a tibial compartment.

8. The method of claim 1, wherein said location is such that a distal portion of said delivery device is close to an interior edge of cortical bone and some other portion of said delivery device is located in or passes through cancellous bone.

9. The method of claim 1, wherein said delivery device is generally parallel to an adjacent portion of said bone-cartilage interface.

10. The method of claim 1, wherein said delivery device is externally threaded and said advancing comprises rotating said delivery device about a longitudinal axis of said delivery device.

11. The method of claim 1, further comprising, after said advancing said delivery device but before said delivering of said bone-cartilage interface therapeutic material, partially retracting said delivery device so as to create an empty space for receiving said bone-cartilage interface therapeutic material, and delivering an amount of said bone-cartilage interface therapeutic material, and optionally repeating said retracting and said delivering.

12. The method of claim 1, wherein said delivery device has at least one side port at or near a distal end thereof, such that said bone-cartilage interface therapeutic material can exit from said delivery device through said side port.

13. The method of claim 1, wherein said introducing said delivery device is performed using imaging guidance, wherein said imaging guidance is selected from the group consisting of fluoroscopy and ultrasound guidance.

14. The method of claim 1, further comprising delivering, at any time during said method, a joint therapeutic material into said peripheral joint between said first and second bones.

15. The method of claim 14, wherein said bone-cartilage interface therapeutic material and said joint therapeutic material are identical to each other.

* * * * *